United States Patent
Hillman et al.

(10) Patent No.: US 6,589,935 B1
(45) Date of Patent: *Jul. 8, 2003

(54) INSULIN RECEPTOR TYROSINE KINASE SUBSTRATE

(75) Inventors: Jennifer L. Hillman, Mountain View, CA (US); Neil C. Corley, Mountain View, CA (US); Karl J. Guegler, Menlo Park, CA (US); Mariah Baughn, San Jose, CA (US)

(73) Assignee: Incyte Genomics, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/046,572

(22) Filed: Mar. 23, 1998

Related U.S. Application Data

(63) Continuation-in-part of application No. 08/878,563, filed on Jun. 19, 1997, now Pat. No. 5,891,674.

(51) Int. Cl.[7] .......................... C12N 15/00; A61K 38/17
(52) U.S. Cl. ..................... 514/12; 435/69.1; 435/320.1; 435/325; 435/252.3; 435/254.1; 536/23.1; 536/23.5; 530/350
(58) Field of Search .............................. 435/69.1, 320.1, 435/325, 252.3, 254.1; 536/23.5, 23.1, 24.3, 24.31; 530/350; 514/12

(56) References Cited

U.S. PATENT DOCUMENTS

| | | | | |
|---|---|---|---|---|
| 5,194,596 A | * | 3/1993 | Tischer | 530/399 |
| 5,350,836 A | * | 9/1994 | Kopchick | 530/399 |
| 5,891,674 A | * | 4/1999 | Hillman | 435/69.1 |

FOREIGN PATENT DOCUMENTS

| | | | |
|---|---|---|---|
| WO | WO94/01548 | * | 1/1994 |

OTHER PUBLICATIONS

Yeh et al., J.Biol.Chem. 271(6):2921–8, Feb. 1996.*
Hillier et al., Accession No. R55195, The WashU–Merck EST project, May 1995.*
Marra et al., Accession No. AA061801 (The Marra M/Mouse EST Project), Sep. 1996.*
Hachiya et al., Genbank Accession No. U70669, Dec. 1997.*
Bowie et al., Science 247:1306–1310, Mar. 1990.*
George et al., Macromolecular sequencing and synthesis, Alan Riss, p. 127–149, 1988.*
White, M.F. and C.R. Kahn, "The Insulin Signaling System", *J. Biol. Chem.*, 269:1–4 (1994).
Almind, K. et al., "A Common Amino Acid Polymorphism in Insulin Receptor Substrate–1 Causes Impaired Insulin Signaling", *J. Clin. Invest.*, 97:2569–2575 (1996).
Yeh, T.C. et al., "Characterization and Cloning of a 58/53–kDa Substrate of the Insulin Receptor Tyrosine Kinase", *J. Biol. Chem.*, 271:2921–2928 (1996).
Stoffel, M. et al., "Human insulin receptor substrate–1 gene (IRS1): chromosomal localization to 2q35–q36.1 and identification of a simple tandem repeat DNA polymorphism", *Diabetologia*, 36:335–337 (1993).
Yeh, T.C. et al., (Direct Submission), GenBank Sequence, Database (Accession U41899), National Center for Biotechnology Information, National Library of Medicine, Bethesda, Maryland, 20894 (GI 1203819; GI 1203820).

* cited by examiner

*Primary Examiner*—Lorraine Spector
*Assistant Examiner*—Eliane Lazar-Wesley

(57) ABSTRACT

The invention provides a human insulin receptor tyrosine kinase substrate (IRS-p53h) and polynucleotides which identify and encode IRS-p53h. The invention also provides expression vectors, host cells, antibodies, agonists, and antagonists. The invention also provides methods for treating or preventing disorders associated with expression of IRS-p53h.

13 Claims, 16 Drawing Sheets

```
5'  GT  CCG  CTT  TCG  TCT  CCG  TCC  TGC  CGT  TAC  CGC  TGC  CGC  CGC  TTG
                                                                            54

CGT  CCC  CCG  CTC  CGG  TCT  GTG  GTG  CAG  CCG  GGA  CCC  AGG  ACC  ATG  TCT  CTG  TCT
                                                                         M    S    L    S
                                                                                        108

CGC  TCA  GAG  GAG  ATG  CAC  CGG  CTC  ACG  GAA  AAT  GTC  TAT  AAG  ATC  ATG  GAG
    R    S    E    E    M    H    R    L    T    E    N    V    Y    K    I    M    E
                                                                                        162

CAG  TTC  AAC  CCT  AGC  CTC  CGG  AAC  TTC  ATC  GCC  ATG  GGG  AAG  AAT  TAC  GAG  AAG
    Q    F    N    P    S    L    R    N    F    I    A    M    G    K    N    Y    E    K
                                                                                        216

GCA  CTG  GCA  GGT  GTG  ACG  TAT  GCA  GCC  AAA  GGC  TAC  TTT  GAC  GCC  CTG  GTG  AAG
    A    L    A    G    V    T    Y    A    A    K    G    Y    F    D    A    L    V    K
                                                                                        270

ATG  GGG  GAG  CTG  GCC  AGC  GAG  AGC  CAG  GGC  TCC  AAA  GAA  CTC  GGA  GAC  GTT  CTC
    M    G    E    L    A    S    E    S    Q    G    S    K    E    L    G    D    V    L
                                                                                        324

TTC  CAG  ATG  GCT  GAA  GTC  CAC  AGG  CAG  ATC  CAG  AAT  CAG  CTG  GAA  GAA  ATG  CTG
    F    Q    M    A    E    V    H    R    Q    I    Q    N    Q    L    E    E    M    L
                                                                                        378
```

FIGURE 1A

|     | 387 |     |     | 396 |     |     | 405 |     |     | 414 |     |     | 423 |     |     | 432 |
| --- | --- | --- | --- | --- | --- | --- | --- | --- | --- | --- | --- | --- | --- | --- | --- | --- |
| AAG | TCT | TTT | CAC | AAC | GAG | CTG | CTT | ACG | CAG | CTG | GAG | CAG | AAG | GTG | GAG | CTG | GAC |
| K   | S   | F   | H   | N   | E   | L   | L   | T   | Q   | L   | E   | Q   | K   | V   | E   | L   | D   |

|     | 441 |     |     | 450 |     |     | 459 |     |     | 468 |     |     | 477 |     |     | 486 |
| --- | --- | --- | --- | --- | --- | --- | --- | --- | --- | --- | --- | --- | --- | --- | --- | --- |
| TCC | AGG | TAT | CTG | AGT | GCT | GCG | CTA | AAG | TAC | CAG | ACT | GAG | CAA | AGG | AGC | AAA |
| S   | R   | Y   | L   | S   | A   | A   | L   | K   | Y   | Q   | T   | E   | Q   | R   | S   | K   |

|     | 495 |     |     | 504 |     |     | 513 |     |     | 522 |     |     | 531 |     |     | 540 |
| --- | --- | --- | --- | --- | --- | --- | --- | --- | --- | --- | --- | --- | --- | --- | --- | --- |
| GGC | GAC | CTG | GAC | AAG | TGT | CAG | GCT | GAG | CTG | AAG | AAG | CTT | CGG | AAG | AAG | AGC |
| G   | D   | L   | D   | K   | C   | Q   | A   | E   | L   | K   | K   | L   | R   | K   | K   | S   |

|     | 549 |     |     | 558 |     |     | 567 |     |     | 576 |     |     | 585 |     |     | 594 |
| --- | --- | --- | --- | --- | --- | --- | --- | --- | --- | --- | --- | --- | --- | --- | --- | --- |
| CAG | AGC | AAG | AAT | CCT | CAG | AAG | TAC | TCG | GAC | AAG | GAG | CTG | CAG | TAC | ATC | GAC |
| Q   | S   | K   | N   | P   | Q   | K   | Y   | S   | D   | K   | E   | L   | Q   | Y   | I   | D   |

|     | 603 |     |     | 612 |     |     | 621 |     |     | 630 |     |     | 639 |     |     | 648 |
| --- | --- | --- | --- | --- | --- | --- | --- | --- | --- | --- | --- | --- | --- | --- | --- | --- |
| GCC | ATC | AGC | AAC | AAG | CAG | GGC | GAG | CTG | GAG | AAT | TAC | GTG | TCC | GAC | TAC | AAG |
| A   | I   | S   | N   | K   | Q   | G   | E   | L   | E   | N   | Y   | V   | S   | D   | Y   | K   |

|     | 657 |     |     | 666 |     |     | 675 |     |     | 684 |     |     | 693 |     |     | 702 |
| --- | --- | --- | --- | --- | --- | --- | --- | --- | --- | --- | --- | --- | --- | --- | --- | --- |
| ACC | CTG | GCA | ACA | GAG | GAG | TGC | AGG | CGC | TTC | TGC | TTG | GAC | GGC | GAG | AAG | CAG | TGC |
| T   | L   | A   | T   | E   | E   | C   | R   | R   | F   | C   | L   | D   | G   | E   | K   | Q   | C   |

|     | 711 |     |     | 720 |     |     | 729 |     |     | 738 |     |     | 747 |     |     | 756 |
| --- | --- | --- | --- | --- | --- | --- | --- | --- | --- | --- | --- | --- | --- | --- | --- | --- |
| GCC | GTG | GCC | AAG | AAC | TCC | GCC | TAC | CAC | TCC | AAG | GGC | TAC | GAG | AAG | CTG | CTG | CCG |
| A   | V   | A   | K   | N   | S   | A   | Y   | H   | S   | K   | G   | Y   | E   | K   | L   | L   | P   |

FIGURE 1B

```
      765              774       783              792              801              810
CAG AAG CTG CCG CTG TGG CAA CAG GCC TGT GCC GAC CCC AGC AAG ATC CCG GAG
 Q   K   L   P   L   W   Q   Q   A   C   A   D   P   S   K   I   P   E 819              828       837              846              855              864
CGC GCG GTG CAG CTC ATG CAG CTC GCC GTG GCC AGC GGC ACC CTC CCC AGC
 R   A   V   Q   L   M   Q   L   A   V   A   S   G   T   L   P   S 873              882       891              900              909              918
GCC CTG TCG GCC TCC AAG TCC AAC CTG GTC ATT TCC GAC CCC ATT CCG GGG GCC
 A   L   S   A   S   K   S   N   L   V   I   S   D   P   I   P   G   A 927              936       945              954              963              972
AAG CCC CTG CCG GTG CCC CCC GAG CTG GCA CCG GCA TTC GTG GGG CGG ATG TCT GCC
 K   P   L   P   V   P   P   E   L   A   P   A   F   V   G   R   M   S   A 981              990       999              1008             1017             1026
CAG GAG AGC ACA CCC ATC ATG AAC GGC GTC ACA GGC CCG GAT GGC GAG GAC TAC
 Q   E   S   T   P   I   M   N   G   V   T   G   P   D   G   E   D   Y 1035             1044      1053             1062             1071             1080
AGC CCG TGG GCT GAC CGC AAG GCT GCC CAG CCC AAA TCC CTG TCT CCT CCG CAG
 S   P   W   A   D   R   K   A   A   Q   P   K   S   L   S   P   P   Q 1089             1098      1107             1116             1125             1134
TCT CAG AGC AAG CTC AGC GAC TCC TAC TCC AAC ACA CTC CCC GTG CGC AAG AGC
 S   Q   S   K   L   S   D   S   Y   S   N   T   L   P   V   R   K   S
```

FIGURE 1C

```
                1143            1152            1161            1170            1179            1188
GTG ACC CCA AAA AAC AGC TAT GCC ACC ACC GAG AAC AAG ACT CTG CCT CGC TCG
 V   T   P   K   N   S   Y   A   T   T   E   N   K   T   L   P   R   S
                1197            1206            1215            1224            1233            1242
AGC TCC ATG GCA GCC GGC CTG GAG CGC AAT GGC CGT ATG CGG GTG AAG GCC ATC
 S   S   M   A   A   G   L   E   R   N   G   R   M   R   V   K   A   I
                1251            1260            1269            1278            1287            1296
TTC TCC CAC GCT GCT GGG GAC AAC AGC ACC CTC AGC TTC AAG GAG GGT GAC
 F   S   H   A   A   G   D   N   S   T   L   S   F   K   E   G   D
                1305            1314            1323            1332            1341            1350
CTC ATT ACC CTG CTG GTG CCT GAG GCC CGC GAT GGC TGG CAC TAC GGA GAG AGT
 L   I   T   L   L   V   P   E   A   R   D   G   W   H   Y   G   E   S
                1359            1368            1377            1386            1395            1404
GAG AAG ACC AAG ATG CGG GGC TGG TTT CCC TTC TCC TAC ACC CGG GTC TTG GAC
 E   K   T   K   M   R   G   W   F   P   F   S   Y   T   R   V   L   D
                1413            1422            1431            1440            1449            1458
AGC GAT GGC AGT GAC AGG CTG CGC ATG AGC CTG CAG CAA GGG AAG AGC AGC
 S   D   G   S   D   R   L   R   M   S   L   Q   Q   G   K   S   S
                1467            1476            1485            1494            1503            1512
ACG GGC AAC CTC CTG GAC AAG GAC GAC CTG GCC AGC CCA CCC GAT TAC GGC
 T   G   N   L   L   D   K   D   D   L   A   S   P   P   D   Y   G
```

FIGURE 1D

```
        1521              1530              1539              1548              1557              1566
GCC GCC TCC CGG GCT TTC CCC GCC CAG ACG GCC AGC GGC TTC AAG CAG AGG CCC
 A   A   S   R   A   F   P   A   Q   T   A   S   G   F   K   Q   R   P 1575              1584              1593              1602              1611              1620
TAC AGT GTG GCC GTG CCC GCC TTC TCC CAG GGC CTG GAT GAC TAT GGA GCG CGG
 Y   S   V   A   V   P   A   F   S   Q   G   L   D   D   Y   G   A   R 1629              1638              1647              1656              1665              1674
TCC ATG AGC AGG AAT CCC TTT GCC CAC GTC CAG CTG AAG CCG ACA GTG ACC AAC
 S   M   S   R   N   P   F   A   H   V   Q   L   K   P   T   V   T   N 1683              1692              1701              1710              1719              1728
GAC AGG TCT GCC CCC CTC AGC CAT CTG CAG GGC CAT TGC CAG TGC TGC CCA TCT
 D   R   S   A   P   L   S   H   L   Q   G   H   C   Q   C   C   P   S 1737              1746              1755              1764              1773              1782
GGT GGC TTC CCC CGC CCT TCC CAT GTA GCC TGT TCT GTC ATC ATC TGT GCG TTC 1791              1800              1809              1818              1827              1836
TGT TGT AGA GAA CAT CCA GGC CCC GGC TGC CTG GTC TTG CCC CAC TTG AGT CTG 1845              1854              1863              1872              1881              1890
GCC TGG ACT GGA TTC CAG CTG TTC TAG GCA GGG CCG GGC AGA GTG GGG CGC AAG 1899              1908              1917              1926              1935              1944
CCC TGG ATG GCG AGA CCC AGT GGC TGG GNC TGC CAG GGC TGA GGG GGC GCT CTT

```
              1953           1962           1971           1980           1989           1998
GAA GGT ACA CGC TCT GGT CAC ATG GCA TGG AGC TTG GGT ACC CTG AGT AAG GGA 2007           2016           2025           2034           2043           2052
GAA TTT GGC CAC TGG TGG CTG GGA GGG AAC TTG TTG CCT GCT GCT CTC CTG CCT 2061           2070           2079
AAT AAA AAG CTC TCC TGC AAA AAA AAA AT 3'
```

FIGURE 1F

```
5'  CG CTT GCT TGG CAT TTG GAC ATC TAC GGC TGG AAT TCC GGG TCG ACC CAC GCG   54
    TCC GGT CCG CTT TCG TCT CCG TCC CCG TAC CGC CGC CGC TGC TGC CGC CGC       108
    TTG CGT CCC CCG CTC CGG TCT GTG CAG CCG GGA CCC AGG ACC ATG TCT CTG       162
                                                                M   S   L
    TCT CGC TCA GAG GAG ATG CAC CGG CTC ACG GAA AAT GTC TAT AAG AGG GTG GAA   216
     S   R   S   E   E   M   H   R   L   T   E   N   V   Y   K   R   V   E
    GAG AAG TAC CAG CGG AAC CTT TTT CCT ATT TTT TCT CCT TCT GCG CTG AAA CCA   270
     E   K   Y   Q   R   N   L   F   P   I   F   S   P   S   A   L   K   P
    GAA AGC AGG AAC TTT CGT GGT GAG AGT TGG CAG GGG ACC ATC ATG GAG CAG TTC   324
     E   S   R   N   F   R   G   E   S   W   Q   G   T   I   M   E   Q   F
    AAC CCT AGC CTC CGG AAC TTC ATC GCC ATG GGG AAG AAT TAC GAG AAG GCA CTG   378
     N   P   S   L   R   N   F   I   A   M   G   K   N   Y   E   K   A   L
```

FIGURE 2A

```
387             396         405         414         423         432
GCA GGT GTG ACG TAT GCA GCC AAA GGC TAC TTT GAC GCC CTG AAG ATG GGG
 A   G   V   T   Y   A   A   K   G   Y   F   D   A   L   K   M   G 441             450         459         468         477         486
GAG CTG GCC AGC GAG CAG AGC TCC AAA GAA CTC GGA GAC GTT CTC TTC CAG
 E   L   A   S   E   Q   S   S   K   E   L   G   D   V   L   F   Q 495             504         513         522         531         540
ATG GCT GAA GTC CAC AGG CAG ATC CAG AAT CAG CTG GAA GAA ATG CTG AAG TCT
 M   A   E   V   H   R   Q   I   Q   N   Q   L   E   E   M   L   K   S 549             558         567         576         585         594
TTT CAC AAC GAG CTT CTT ACG CAG CTG GAG CAG AAG GTG GAG CTG GAC TCC AGG
 F   H   N   E   L   L   T   Q   L   E   Q   K   V   E   L   D   S   R 603             612         621         630         639         648
TAT CTG AGT GCT GCG CTG AAG AAA TAC CAG ACT GAG CAA AGG AGC AAA GGC GAC
 Y   L   S   A   A   L   K   K   Y   Q   T   E   Q   R   S   K   G   D 657             666         675         684         693         702
GCC CTG GAC AAG TGT CAG GCT GAG CTG AAG AAG CTT CGG AAG AAG AGC CAG GGC
 A   L   D   K   C   Q   A   E   L   K   K   L   R   K   K   S   Q   G 711             720         729         738         747         756
AGC AAG AAT CCT CAG AAG TAC TCG GAC AAG GAG CTG CAG TAC ATC GAC GCC ATC
 S   K   N   P   Q   K   Y   S   D   K   E   L   Q   Y   I   D   A   I
```

FIGURE 2B

|     |     |     |     |     |     |     |     |     |
|-----|-----|-----|-----|-----|-----|-----|-----|-----|
| | 765 | | 774 | 783 | 792 | 801 | | 810 |
| AGC | AAG | CAG | GGC | GAG | CTG | GAG | AAT | TAC | GTG | TCC | GAC | GGC | TAC | AAG | ACC | GCA |
| S | N | K | Q | G | E | L | E | N | Y | V | S | D | G | Y | K | T | A |

(Reconstructing as sequential codon/AA blocks)

FIGURE 2C

```
      765                 774           783           792           801                 810
AGC  AAG  CAG  GGC       GAG  CTG       GAG  AAT      TAC  GTG     TCC  GAC  GGC       TAC  AAG  ACC  GCA
 S    N    K    Q         E    L         E    N        Y    V       S    D    G         Y    K    T    A 819                 828           837           846           855                 864
CTG  ACA  GAG  GAG       CGC  AGG       CGC  TTC      TGC  TTC      CTG  GTG  GAG       AAG  CAG  TGC  GCC  GTG
 L    T    E    E         R    R         R    F        C    F        L    V    E         K    Q    C    A    V 873                 882           891           900           909                 918
GCC  AAG  TCC  GCG       TAC  CAC       TCC  AAG      GGC  AAG      GAG  CTG  CCG       CAG  AAG
 A    K    S    A         Y    H         S    K        G    K        E    L    P         Q    K 927                 936           945           954           963                 972
CTG  CCG  CTG  TGG       CAG  GCC       TGT  GCC      CAG  GTG      GAG  CTG  CCG       GAG  CGC  GCG
 L    P    L    W         Q    A         C    A        Q    V        E    L    P         E    R    A 981                 990           999           1008          1017                1026
GTG  CAG  CTC  ATG       CAG  GTG       GCC  AGC      AAC  GGC      ACC  CTC  CCC       AGC  GCC  CTG
 V    Q    L    M         Q    V         A    S        N    G        T    L    P         S    A    L 1035                1044          1053          1062          1071                1080
TCG  GCC  TCC  AAG       TCC  AAC       ATT  TCC      GAC  CCC      GCC  ACC  CTC       CCG  AAG  CCC
 S    A    S    K         S    N         I    S        D    P        A    T    L         P    K    P 1089                1098          1107          1116          1125                1134
CTG  CCG  GTG  CCC       CCC  GAG       GCA  CCG      TTC  GTG      GGG  CGG  ATG       TCT  GCC  CAG  GAG
 L    P    V    P         P    E         A    P        F    V        G    R    M         S    A    Q    E
```

FIGURE 2C

```
                 1143            1152            1161            1170            1179            1188
          AGC ACA CCC ATC ATG AAC GGC GTC ACA GGC CCG GAT GGC GAG GAC TAC AGC CCG
           S   T   P   I   M   N   G   V   T   G   P   D   G   E   D   Y   S   P 1197            1206            1215            1224            1233            1242
          TGG GCT GAC CGC AAG GCT GCC CAG CCC AAA TCC CTG TCT CCT CCG CAG TCT CAG
           W   A   D   R   K   A   A   Q   P   K   S   L   S   P   P   Q   S   Q 1251            1260            1269            1278            1287            1296
          AGC AAG CTC AGC GAC TCC TAC TCC AAC ACA CTC CCC GTG CGC AAG AGC GTG ACC
           S   K   L   S   D   S   Y   S   N   T   L   P   V   R   K   S   V   T 1305            1314            1323            1332            1341            1350
          CCA AAA AAC AGC TAT GCC ACC ACC GAG AAC AAG ACT CTG CCT CGC TCG AGC TCC
           P   K   N   S   Y   A   T   T   E   N   K   T   L   P   R   S   S   S 1359            1368            1377            1386            1395            1404
          ATG GCA GCC GGG GAC CTG GAG CGC AAT GGC CGT ATG CGG GTG AAG GCC ATC TTC TCC
           M   A   A   G   D   L   E   R   N   G   R   M   R   V   K   A   I   F   S 1413            1422            1431            1440            1449            1458
          CAC GCT GCT GGG GAC AAC AGC ACC CTC CTG AGC TTC AAG GAG GGT GAC CTC ATT
           H   A   A   G   D   N   S   T   L   L   S   F   K   E   G   D   L   I 1467            1476            1485            1494            1503            1512
          ACC CTG GTG CCT GAG GCC CGC GAT GGC TGG CAC TAC GGA GAG AGT GAG AAG
           T   L   V   P   E   A   R   D   G   W   H   Y   G   E   S   E   K
```

FIGURE 2D

```
     1521           1530           1539          1548           1557           1566
ACC AAG ATG CGG GGC TGG TTT CCC TTC TCC TAC ACC CGG GTC TTG GAC AGC GAT
 T   K   M   R   G   W   F   P   F   S   Y   T   R   V   L   D   S   D 1575           1584           1593          1602           1611           1620
GGC AGT GAC AGG CTG CAC ATG AGC CTG CAG CAA GGG AAG AGC AGC ACG GGC
 G   S   D   R   L   H   M   S   L   Q   Q   G   K   S   S   T   G 1629           1638           1647          1656           1665           1674
AAC CTC CTG GAC AAG GAC GAC CTG GCC ATC CCA CCC GAT TAC GGC GCC GCC
 N   L   L   D   K   D   D   L   A   I   P   P   D   Y   G   A   A 1683           1692           1701          1710           1719           1728
TCC CGG GCC TTC CCC CAG ACG GCC AGC GGC TTC AAG CAG AGG CCC TAC AGT
 S   R   A   F   P   Q   T   A   S   G   F   K   Q   R   P   Y   S 1737           1746           1755          1764           1773           1782
GTG GCC GTG CCC GCC TTC TCC CAG GGC CTG GAT GAT TAT GGA GCG CGG TCC ATG
 V   A   V   P   A   F   S   Q   G   L   D   D   Y   G   A   R   S   M 1791           1800           1809          1818           1827           1836
AGC AGC GAT GTG GAA GTG GCC AGA TTC TGA GCC GCC TGA CTA GAG TTA GAA
 S   S   A   D   V   E   V   A   R   F   *   A   A   *   L   E   L   E 1845           1854           1863          1872           1881           1890
TCC CTT TGC CCA CGT CCA GCT GAA GCC GAC AGT GAC CAA CGA CAG GTC TGC CCC
```

FIGURE 2E

```
     1899      1908      1917      1926      1935      1944
CCT CCT CAG CTG ATG GCC ACA TCT GCA GTG CTG CCC ATC TGG TGG CTT CCC CCG
     1953      1962      1971      1980      1989      1998
CCC TTC CCA TGT AGC CTG TTC TGT CAT CAT CTG TGC GTT CCT GTG TAG AGA ACA
     2007      2016      2025      2034      2043      2052
TCC AGG CCC CGG CTG CCT GGT CTT GCC CCA CTT GAG TCT GGC CTG GAC TGG ATC
     2061      2070      2079      2088      2097      2106
CCA GCT GTT CTA GGC AGG GCC GGG CAG AGT GGG GCG CAG GCC CCT GAA GGG CGA
     2115      2124      2133      2142      2151      2160
GAC CCA GTG GCT GGG CTG CCC AGG GCT GAG GGG CCG CCT CTT GAG GGT ACA CGC
     2169      2178      2187      2196      2205      2214
CTC TGG TCA CAT GGA GCC CAT GGA GCC TTG GGT ACC CCT GAG TTA AGG GAG GAC ATT
     2223      2232      2241      2250      2259      2268
TGG CCA GCT GGT GGC TGG GAG GGG AGC CTG GCC CTG CTT CTC CTG CCT
     2277      2286      2295      2304      2313      2322
AAT AAA CAG GCT TCT CCT GCA AAA AAA AAA AAA AGA AAA AAG AGA GGA GGG

AGA GGA T 3'
```

| | | |
|---|---|---|
| 327 | P Q S Q S K L S D S Y S N T L P V R K S | 918158 |
| 360 | P Q S Q S K L S D S Y S N T L P V R K S | 2493150 |
| 328 | P Q S Q S K L S D S Y S N T L P V R K S | GI 1203820 |
| | | |
| 347 | V T P K N S Y A T T E N K T L P R S S S | 918158 |
| 380 | V T P K N S Y A T T E N K T L P R S S S | 2493150 |
| 348 | V T P K N S Y A T T E N K T L P R S S S | GI 1203820 |
| | | |
| 367 | M A A G L E R N G R M R V K A I F S H A | 918158 |
| 400 | M A A G L E R N G R M R V K A I F S H A | 2493150 |
| 368 | M A A G L E R N G R M R V K A I F S H A | GI 1203820 |
| | | |
| 387 | A G D N S T L L S F K E G D L I T L L V | 918158 |
| 420 | A G D N S T L L S F K E G D L I T L L V | 2493150 |
| 388 | A G D N S T L L S F K E G D L I T L L V | GI 1203820 |
| | | |
| 407 | P E A R D G W H Y G E S E K T K M R G W | 918158 |
| 440 | P E A R D G W H Y G E S E K T K M R G W | 2493150 |
| 408 | P E A R D G W H Y G E S E K T K M R G W | GI 1203820 |
| | | |
| 427 | F P F S Y T R V L D S D G S D R L R M S | 918158 |
| 460 | F P F S Y T R V L D S D G S D R L H M S | 2493150 |
| 428 | F P F S Y T R V L D S D G S D R L H M S | GI 1203820 |
| | | |
| 447 | L Q Q G K S S S T G N L L D K D D L A S | 918158 |
| 480 | L Q Q G K S S S T G N L L D K D D L A I | 2493150 |
| 448 | L Q Q G K S S S T G N L L D K D D L A V | GI 1203820 |
| | | |
| 467 | P P P D Y G A A S R A F P A Q T A S G F | 918158 |
| 500 | P P P D Y G A A S R A F P A Q T A S G F | 2493150 |
| 468 | P P P D Y G T S S R A F P T Q T A G T F | GI 1203820 |
| | | |
| 487 | K Q R P Y S V A V P A F S Q G L D D Y G | 918158 |
| 520 | K Q R P Y S V A V P A F S Q G L D D Y G | 2493150 |
| 488 | K Q R P Y S V A V P A F S Q G L D D Y G | GI 1203820 |

FIGURE 3D ically distinct
INSULIN RECEPTOR TYROSINE KINASE SUBSTRATE

This application is a continuation-in-part of U.S. application Ser. No. 08/878,563 filed Jun. 19, 1997, now U.S. Pat. No. 5,891,674.

FIELD OF THE INVENTION

This invention relates to nucleic acid and amino acid sequences of two human insulin receptor tyrosine kinase substrates and to the use of these sequences in the diagnosis, prevention, and treatment of reproductive disorders, Alzheimer's disease, cancer, immunological disorders, and disorders associated with insulin response.

BACKGROUND OF THE INVENTION

Insulin controls blood glucose levels by stimulating glucose influx and metabolism in muscle and adipocytes and by inhibiting gluconeogenesis in the liver. Insulin also modifies the expression or the activity of a variety of enzymes and transport systems in nearly all cells.

Insulin action is mediated through the insulin receptor (IR), a transmembrane glycoprotein with protein tyrosine kinase (PTK) activity. Insulin binding triggers receptor autophosphorylation which activates PTK activity. The cellular response to insulin is mediated through tyrosine phosphorylation of cytosolic polypeptide substrates which act as second messengers in IR signal transduction. Once phosphorylated, the substrates bind to and activate various signal transduction proteins. The signal transduction proteins contain Src-homology-2 (SH2)-domains which bind phosphotyrosine-containing peptide motifs.

Several IR-PTK substrates have been described. The most extensively characterized substrate is the 185-kDa insulin receptor substrate-1 (IRS-1). IRS-1 is found in a variety of insulin responsive cells and tissues. It exhibits no intrinsic enzyme activity but, once phosphorylated, binds to and activates SH2-containing signal transduction proteins including phosphatidylinositol (PI) 3'-kinase and GRB-2, a regulator of the Ras pathway. (White, M. F. et al. (1994) J. Biol. Chem. 269:1–4.) Mutations in the IRS-1 gene impairs insulin-stimulated signaling and may contribute to insulin resistance in normal and diabetic populations. (Almind, K. et al. (1996) J. Clin. Invest. 97:2569–2575.)

Two 60-kDa protein substrates of the IR-PTK have been identified. One associates with the GTPase activator of Ras (termed GAP) and the other associates with PI 3'-kinase. (Yeh, T. et al. (1996) J. Biol. Chem. 271:2921–2928.) Two additional substrates for IR-PTK with molecular masses of 53 and 58 kDa were recently identified in rodents. These proteins, p53 and p58, are closely related and may arise from alternative splicing of mRNA or differential post-translational modifications. P53 and p58 do not associate with GAP or PI 3'-kinase and are immunologically distinct from the 60-kDa GAP-associated protein and the 60-kDa PI 3'-kinase-associated protein. P53 contains a microbodies C-terminal targeting signal which enables import of the protein into peroxisomes, glyoxysomes, and glycosomes. (Yeh, et al., supra.)

Post-receptor defects in the insulin signaling pathway are a common feature of type 2 (non-insulin-dependent) diabetes mellitus. (Stoffel M. et al. (1993) Diabetologia 36: 335–337.) Other disorders or conditions associated with disturbances in insulin response include hyperglycemia, myotonic muscular dystrophy, acanthosis nigricans, retinopathy, nephropathy, atherosclerotic coronary and peripheral arterial disease, and peripheral and autonomic neuropathies.

The discovery of two new human insulin receptor tyrosine kinase substrates and the polynucleotides encoding them satisfies a need in the art by providing new compositions which are useful in the diagnosis, prevention and treatment of reproductive disorders, Alzheimer's disease, cancer, immunological disorders, and disorders associated with insulin response.

SUMMARY OF THE INVENTION

The invention features substantially purified polypeptides comprising the amino acid sequence of SEQ ID NO:1 or SEQ ID NO:3 or a fragment of SEQ ID NO:1 or SEQ ID NO:3.

The invention further provides a substantially purified variant having at least 90% amino acid sequence identity to the amino acid sequence of SEQ ID NO:1 or SEQ ID NO:3 or a fragment of SEQ ID NO:1 or SEQ ID NO:3. The invention also provides an isolated and purified polynucleotide encoding the polypeptide comprising the sequence of SEQ ID NO:1 or SEQ ID NO:3 or a fragment of SEQ ID NO:1 or SEQ ID NO:3. The invention also includes an isolated and purified polynucleotide variant having at least 90% polynucleotide sequence identity to the polynucleotide encoding the polypeptide comprising the amino acid sequence of SEQ ID NO:1 or SEQ ID NO:3 or a fragment of SEQ ID NO:1 or SEQ ID NO:3.

The invention further provides an isolated and purified polynucleotide which hybridizes under stringent conditions to the polynucleotide encoding the polypeptide comprising the amino acid sequence of SEQ ID NO:1 or SEQ ID NO:3 or a fragment of SEQ ID NO:1 or SEQ ID NO:3, as well as an isolated and purified polynucleotide which is complementary to the polynucleotide encoding the polypeptide comprising the amino acid sequence of SEQ ID NO:1 or SEQ ID NO:3 or a fragment of SEQ ID NO:1 or SEQ ID NO:3.

The invention also provides an isolated and purified polynucleotide comprising the polynucleotide sequence of SEQ ID NO:2 and SEQ ID NO:4 or a fragment of SEQ ID NO:2 and SEQ ID NO:4, and an isolated and purified polynucleotide variant having at least 90% polynucleotide sequence identity to the polynucleotide comprising the polynucleotide sequence of SEQ ID NO:2 and SEQ ID NO:4 or a fragment of SEQ ID NO:2 and SEQ ID NO:4. The invention also provides an isolated and purified polynucleotide having a sequence complementary to the polynucleotide comprising the polynucleotide sequence of SEQ ID NO:2 and SEQ ID NO:4 or a fragment of SEQ ID NO:2 and SEQ ID NO:4.

The invention further provides an expression vector containing at least a fragment of the polynucleotide encoding the polypeptide comprising the sequence of SEQ ID NO:1 or SEQ ID NO:3 or a fragment of SEQ ID NO:1 or SEQ ID NO:3. In another aspect, the expression vector is contained within a host cell.

The invention also provides a method for producing a polypeptide comprising the amino acid sequence of SEQ ID NO:1 or SEQ ID NO:3 or a fragment of SEQ ID NO:1 or SEQ ID NO:3, the method comprising the steps of: (a) culturing the host cell containing an expression vector containing at least a fragment of a polynucleotide encoding the polypeptide comprising the amino acid sequence of SEQ ID NO:1 or SEQ ID NO:3 or a fragment of SEQ ID NO:1 or SEQ ID NO:3 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or SEQ ID NO:3 or a fragment of SEQ ID NO:1 or SEQ ID NO:3 in conjunction with a suitable pharmaceutical carrier.

The invention further includes a purified antibody which binds to a polypeptide comprising the sequence of SEQ ID NO:1 or SEQ ID NO:3 or a fragment of SEQ ID NO:1 or SEQ ID NO:3, as well as a purified agonist and a purified antagonist of the polypeptide.

The invention also provides a method for treating or preventing a disorder associated with insulin response, the method comprising administering to a subject in need of such treatment an effective amount of a pharmaceutical composition comprising substantially purified polypeptide having the amino acid sequence of SEQ ID NO:1 or SEQ ID NO:3 or a fragment of SEQ ID NO:1 or SEQ ID NO:3.

The invention also provides a method for treating or preventing a reproductive disorder, the method comprising administering to a subject in need of such treatment an effective amount of an antagonist of the polypeptide having the amino acid sequence of SEQ ID NO:1 or SEQ ID NO:3 or a fragment of SEQ ID NO:1 or SEQ ID NO:3.

The invention also provides a method for treating or preventing Alzheimer's disease, the method comprising administering to a subject in need of such treatment an effective amount of an antagonist of the polypeptide having the amino acid sequence of SEQ ID NO:1 or SEQ ID NO:3 or a fragment of SEQ ID NO:1 or SEQ ID NO:3.

The invention also provides a method for treating or preventing a cancer, the method comprising administering to a subject in need of such treatment an effective amount of an antagonist of the polypeptide having the amino acid sequence of SEQ ID NO:1 or SEQ ID NO:3 or a fragment of SEQ ID NO:1 or SEQ ID NO:3.

The invention also provides a method for treating or preventing an immunological disorder, the method comprising administering to a subject in need of such treatment an effective amount of an antagonist of the polypeptide having the amino acid sequence of SEQ ID NO:1 or SEQ ID NO:3 or a fragment of SEQ ID NO:1 or SEQ ID NO:3.

The invention also provides a method for detecting a polynucleotide encoding a polypeptide comprising the amino acid sequence of SEQ ID NO:1 or SEQ ID NO:3 or a fragment of SEQ ID NO:1 or SEQ ID NO:3 in a biological sample containing nucleic acids, the method comprising the steps of: (a) hybridizing the complement of the polynucleotide encoding the polypeptide comprising the amino acid sequence of SEQ ID NO:1 or SEQ ID NO:3 or a fragment of SEQ ID NO:1 or SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO:1 or SEQ ID NO:3 or a fragment of SEQ ID NO:1 or SEQ ID NO:3 in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of IRS-p53h-1. The alignment was produced using MacDNASIS PRO™ software (Hitachi Software Engineering Co. Ltd. San Bruno, Calif.).

FIGS. 2A, 2B, 2C, 2D, 2E, and 2F show the amino acid sequence (SEQ ID NO:3) and nucleic acid sequence (SEQ ID NO:4) of IRS-p53h-2. The alignment was produced using MacDNASIS PRO™ software (Hitachi Software Engineering Co. Ltd., San Bruno, Calif.).

FIGS. 3A, 3B, 3C, and 3D show the amino acid sequence alignments among IRS-p53h-1 (918158; SEQ ID NO:1 ), IRS-p53h-2 (2493150; SEQ ID NO:3), and IRS p53 from hamster (GI 1203820; SEQ ID NO:5), produced using the multisequence alignment program of LASERGENE™ software (DNASTAR Inc. Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"IRS-p53h," as used herein, refers to the amino acid sequences of substantially purified IRS-p53h obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to IRS-p53h, increases or prolongs the duration of the effect of IRS-p53h. Agonists may include proteins, nucleic acids, carbohydrates, or any other molecules which bind to and modulate the effect of IRS-p53h.

An "allele" or an "allelic sequence," as these terms are used herein, is an alternative form of the gene encoding IRS-p53h. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding IRS-p53h, as described herein, include those sequences with deletions, insertions, or substitutions of different nucleotides, resulting in a polynucleotide the same IRS-p53h or a polypeptide with at least one functional characteristic of IRS-p53h. Included within this definition are polymorphisms which may or may not be readily detectable using a particular oligonucleotide probe of the polynucleotide encoding IRS-p53h, and improper or unexpected hybridization to alleles, with a locus other than the normal chromosomal locus for the polynucleotide sequence encoding IRS-p53h. The encoded protein may also be "altered," and may contain deletions, insertions, or substitutions of amino acid residues which produce a silent change and result in a functionally equivalent IRS-p53h. Deliberate amino acid substitutions may be made on the basis of similarity in polarity, charge, solubility, hydrophobicity, hydrophilicity, and/or the amphipathic nature of the residues, as long as the biological or immunological activity of IRS-p53h is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of IRS-p53h which are preferably about 5 to about 15 amino acids in length and which retain some biological activity or immunological activity of IRS-p53h. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual*, Cold Spring Harbor Press, Plainview, N.Y., pp. 1–5.)

The term "antagonist," as it is used herein, refers to a molecule which, when bound to IRS-p53h, decreases the amount or the duration of the effect of the biological or immunological activity of IRS-p53h. Antagonists may include proteins, nucleic acids, carbohydrates, antibodies, or any other molecules which decrease the effect of IRS-p53h.

As used herein, the term "antibody" refers to intact molecules as well as to fragments thereof, such as Fa, F(ab')$_2$, and Fv fragments, which are capable of binding the epitopic determinant. Antibodies that bind IRS-p53h polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic IRS-p53h, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding IRS-p53h or fragments of IRS-p53h may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding IRS-p53h, by northern analysis is indicative of the presence of nucleic acids encoding IRS-p53h in a sample, and thereby correlates with expression of the transcript from the polynucleotide encoding IRS-p53h.

A "deletion," as the term is used herein, refers to a change in the amino acid or nucleotide sequence that results in the absence of one or more amino acid residues or nucleotides.

The term "derivative," as used herein, refers to the chemical modification of IRS-p53h, of a polynucleotide sequence encoding IRS-p53h, or of a polynucleotide sequence complementary to a polynucleotide sequence encoding IRS-p53h. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program to (DNASTAR, Inc., Madison Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with immunological disorders, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of IRS-p53h. For example, modulation may cause an increase or a decrease in protein activity, binding characteristics, or any other biological, functional, or immunological properties of IRS-p53h.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The terms "operably associated" or "operably linked," as used herein, refer to functionally related nucleic acid sequences. A promoter is operably associated or operably linked with a coding sequence if the promoter controls the transcription of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The team "sample," as used herein, is used in its broadest sense. A biological sample suspected of containing nucleic acids encoding IRS-p53h, or fragments thereof, or IRS-p53h itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization conditions at 42° C. in 50% formamide, 5×SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of IRS-p53h, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The Invention

The invention is based on the discovery of two new human insulin receptor tyrosine kinase substrates (collectively referred to as IRS-p53h, and individually as IRS-p53h-1 and IRS-p53h-2), the polynucleotides encoding IRS-p53h, and the use of these compositions for the diagnosis, treatment, or prevention of reproductive disorders, Alzheimer's disease, cancer, immunological disorders, and disorders associated with insulin response.

Nucleic acids encoding the IRS-p53h-1 of the present invention were first identified in Incyte Clone 918158 from a carcinoma-associated breast tissue cDNA library (BRSTNOT04) using a computer search for amino acid sequence alignments. A consensus sequence, SEQ ID NO:2, was derived from the following overlapping and/or extended nucleic acid sequences: Incyte Clones 918158 (BRSTNOT04), 1342719 (COLNTUT03), and 1522281 (BLADTUT04).

Nucleic acids encoding the IRS-p53h-2 of the present invention were first identified in Incyte Clone 2493150 from the adrenal cDNA library (ADRETUT05) using a computer search for amino acid sequence alignments. A consensus sequence. SEQ ID NO:4, was derived from the following overlapping and/or extended nucleic acid sequences: Incyte Clones 2493150 (ADRETUT05), 918158 (BRSTNOT04), 1520586 and 1522281 (BLADTUT04), 1989307 (CORPNOT02), 1263953 (SYNORAT05), and 1466687 (PANCTUT02).

In one embodiment, the invention encompasses a polypeptide comprising the amino acid sequence of SEQ ID NO:1, as shown in FIGS. 1A, 1B, 1C, 1D, 1E, and 1F. IRS-p53h-1 is 534 amino acids in length and contains two potential N-glycosylation sites at residues N358 and N390; one potential cAMP- and cGMP-dependent protein kinase phosphorylation site at residue S148; eight potential casein kinase II phosphorylation sites at residues S4, T19, T103, S129, S158, S291, T303, and S395; seven potential protein kinase C phosphorylation sites at residues S27, S158, S169, T348, S395, S418, and S440; and three potential tyrosine kinase phosphorylation sites at residues Y17, Y115, and Y178. As shown in FIGS. 3A, 3B, 3C, and 3D, IRS-p53h-1 has chemical and structural homology with IRS p53 from hamster (GI 1203820; SEQ ID NO:5). In particular, IRS-p53h-1 and hamster IRS p53 share 93% amino acid sequence identity, the two potential N-glycosylation sites, the potential cAMP- and cGMP-dependent protein kinase phosphorylation site, seven potential casein kinase II phosphorylation sites, seven potential protein kinase C phosphorylation sites, and three potential tyrosine kinase phosphorylation sites. A fragment of SEQ ID NO:2 from about nucleotide 1621 to about nucleotide 1647 is useful for designing oligonucleotides or to be used directly as a hybridization probe. Northern analysis shows the expression of IRS-ps3h-1 in various tissues, at least 57% of which are immortalized or cancerous and at least 19% of which involve immune response. Of particular note is the expression of IRS-p53h-1 in reproductive, brain, and gastrointestinal tissues, and in Alzheimer's disease.

In another embodiment, the invention encompasses a polypeptide comprising the amino acid sequence of SEQ ID NO:3, as shown in FIGS. 2A, 2B, 2C, 2D, 2E, and 2F. IRS-p53h-2 is 553 amino acids in length and has two potential N-glycosylation sites at residues N391 and N423; one potential cAMP- and cGMP-dependant protein kinase phosphorylation site at residue S181; nine potential casein kinase II phosphorylation sites at residues S4, T52, T136, S162, S191, S324, T336, S428, and S544; seven potential protein kinase C phosphorylation sites at residues S60, S191, S202, T381, S428, S451, and S473; four potential tyrosine kinase phosphorylation sites at residues Y17, Y24, Y148, and Y211; and a microbodies C-terminal targeting signal from about residue A551 to about residue F553. As shown in FIGS. 3A, 3B, 3C, and 3D, IRS-p53h-2 has chemical and structural homology with IRS-p53h-1, and are considered to be splice variants. In addition, as shown in FIGS. 3A, 3B, 3C, and 3D, IRS-p53h-2 has chemical and structural homology with IRS-p53 from hamster (GI 1203820; SEQ ID NO:5). In particular, IRS-p53h-2 and IRS-p53 from hamster share 90% identity, the two potential N-glycosylation sites, the potential cAMP- and cGMP-dependent protein kinase phosphorylation site, seven potential casein kinase II phosphorylation sites, seven potential protein kinase C phosphorylation sites, three potential tyrosine kinase phosphorylation sites; and the microbodies C-terminal targeting signal. A fragment of 4 from about nucleotide 295 to about nucleotide 315 is useful for designing oligonucleotides or to be used directly as a hybridization probe. Northern analysis shows the expression of this sequence in various libraries, at least 61% of which are immortalized or cancerous and at least 14% of which involve immune response. Of particular note is the expression of IRS-p53h-2 in reproductive, brain, gastrointestinal, lung tissues, and in Alzheimer's disease.

The invention also encompasses IRS-p53h variants. A preferred IRS-p53h variant is one which has at least about 80%, more preferably at least about 90%, and most preferably at least about 95% amino acid sequence identity to the IRS-p53h amino acid sequence, and which contains at least one functional or structural characteristic of IRS-p53h.

The invention also encompasses polynucleotides which encode IRS-p53h. In a particular embodiment, the invention encompasses a polynucleotide sequence comprising the sequence of SEQ ID NO:2, which encodes an IRS-p53h, as shown in FIGS. 1A, 1B, 1C, 1D, 1E, and 1F. In a further embodiment, the invention encompasses the polynucleotide sequence comprising the sequence of SEQ ID NO:4, as shown in FIGS. 2A, 2B, 2C, 2D, 2E, and 2F.

The invention also encompasses a variant of a polynucleotide sequence encoding IRS-p53h. In particular, such a variant polynucleotide sequence will have at least about 80%, more preferably at least about 90%, and most preferably at least about 95% polynucleotide sequence identity to the polynucleotide sequence encoding IRS-p53h. A particular aspect of the invention encompasses a variant of SEQ ID NO:2 which has at least about 80%, more preferably at least about 90%, and most preferably at least about 95% polynucleotide sequence identity to SEQ ID NO:2. The invention further encompasses a polynucleotide variant of SEQ ID NO:4 having at least about 80%, more preferably at least about 90%, and most preferably at least about 95% polynucleotide sequence identity to SEQ ID NO:4. Any one of the polynucleotide variants described above can encode an amino acid sequence which contains at least one functional or structural characteristic of IRS-p53h.

It will be appreciated by those skilled in the art that as a result of the degeneracy of the genetic code, a multitude of polynucleotide sequences encoding IRS-p53h, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring IRS-p53h, and all such variations are to be considered as being specifically disclosed.

Although nucleotide sequences which encode IRS-p53h and its variants are preferably capable of hybridizing to the nucleotide sequence of the naturally occurring IRS-p53h under appropriately selected conditions of stringency, it may be advantageous to produce nucleotide sequences encoding IRS-p53h or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding IRS-p53h and its derivatives without altering the encoded amino acid sequences include the production of RNA transcripts having more desirable properties, such as a greater half-life, than transcripts produced from the naturally occurring sequence.

The invention also encompasses production of DNA sequences which encode IRS-p53h and IRS-p53h derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding IRS-p53h or any fragment thereof.

Also encompassed by the invention are polynucleotide sequences that are capable of hybridizing to the claimed polynucleotide sequences, and, in particular, to those shown in SEQ ID NO:2, SEQ ID NO:4, a fragment of SEQ ID NO:2, or a fragment of SEQ ID NO:4, under various conditions of stringency. (See, e.g., Wahl, G. M. and S. L. Berger (1987) Methods Enzymol. 152:399–407; Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, Sequenase® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System (Gibco/BRL, Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding IRS-p53h may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer which is complementary to a linker sequence within the vector and a primer specific to a region of the nucleotide sequence. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 Primer Analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode IRS-p53h may be used in recombinant DNA molecules to direct expression of IRS-p53h, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express IRS-p53h.

As will be understood by those of skill in the art, it may be advantageous to produce IRS-p53h-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter IRS-p53h-encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding IRS-p53h may be ligated to a heterologous sequence to encode a fusion protein. For example, to screen peptide libraries for inhibitors of IRS-p53h activity, it may be useful to encode a chimeric IRS-p53h protein that can be recognized by a commercially available antibody. A fusion protein may also be engineered to contain a cleavage site located between the IRS-p53h encoding sequence and the heterologous protein sequence, so that IRS-p53h may be cleaved and purified away from the heterologous moiety.

In another embodiment, sequences encoding IRS-p53h may be synthesized, in whole or in part, using chemical methods well known in the art. (See, e.g., Caruthers, M. H. et al. (1980) Nucl. Acids Symp. Ser. 7:215–223, and Horn, T. et al. (1980) Nucl. Acids Symp. Ser. 7:225–232.)

Alternatively, the protein itself may be produced using chemical methods to synthesize the amino acid sequence of IRS-p53h, or a fragment thereof. For example, peptide synthesis can be performed using various solid-phase techniques. (See, e.g., Roberge, J. Y. et al. (1995) Science 269:202–204.) Automated synthesis may be achieved using the ABI 431A Peptide Synthesizer (Perkin Elmer). Additionally, the amino acid sequence of IRS-p53h, or any part thereof, may be altered during direct synthesis and/or combined with sequences from other proteins, or any part thereof, to produce a variant polypeptide.

The peptide may be substantially purified by preparative high performance liquid chromatography. (See, e.g. Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties*, WH Freeman and Co., New York, N.Y.)

In order to express a biologically active IRS-p53h, the nucleotide sequences encoding IRS-p53h or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding IRS-p53h and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview, N.Y., ch. 4, 8, and 16–17; and Ausubel, F. M. et al. (1995, and periodic supplements) *Current Protocols in Molecular Biology*, John Wiley & Sons, New York, N.Y., ch. 9, 13, and 16.)

A variety of expression vector/host systems may be utilized to contain and express sequences encoding IRS-p53h. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions, e.g., enhancers, promoters, and 5' and 3' untranslated regions, of the vector and polynucleotide sequences encoding IRS-p53h which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters, e.g., hybrid lacZ promoter of the Bluescript® phagemid (Stratagene, La Jolla, Calif.) or pSport1™ plasmid (Gibco/BRL), may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding IRS-p53h, vectors based on SV40 or EBV may be used with an appropriate selectable marker.

In bacterial systems, a number of expression vectors may be selected depending upon the use intended for IRS-p53h. For example, when large quantities of IRS-p53h are needed for the induction of antibodies, vectors which direct high level expression of fusion proteins that are readily purified may be used. Such vectors include, but are not limited to, multifunctional *E. coli* cloning and expression vectors such as Bluescript® (Stratagene), in which the sequence encoding IRS-p53h may be ligated into the vector in frame with sequences for the amino-terminal Met and the subsequent 7 residues of β-galactosidase so that a hybrid protein is produced, and pIN vectors. (See, e.g., Van Heeke, G. and S. M. Schuster (1989) J. Biol. Chem. 264:5503–5509.) pGEX vectors (Amersham Pharmacia Biotech, Uppsala, Sweden) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding IRS-p53h may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express IRS-p53h. For example, in one such system, *Autographa californica* nuclear polyhedrosis virus (AcNPV) is used as a vector to express foreign genes in *Spodoptera frugiperda* cells or in Trichoplusia larvae. The sequences encoding IRS-p53h may be cloned into a non-essential region of the virus, such as the polyhedrin gene, and placed under control of the polyhedrin promoter. Successful insertion of sequences encoding IRS-p53h will render the polyhedrin gene inactive and produce recombinant virus lacking coat protein. The recombinant viruses may then be used to infect, for example, *S. frugiperda* cells or Trichoplusia larvae in which IRS-p53h may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding IRS-p53h may be ligated into an adenovirus transcription/translation complex consisting of the late promoter and tripartite leader sequence. Insertion in a non-essential E1 or E3 region of the viral genome may be used to obtain a viable virus which is capable of expressing IRS-p53h in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding IRS-p53h. Such signals include the ATG initiation codon and adjacent sequences. In cases where sequences encoding IRS-p53h and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing IRS-p53h can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Visible markers, e.g., anthocyanins, β glucuronidase and its substrate GUS, luciferase and its substrate luciferin may be used. Green fluorescent proteins (GFP) (Clontech, Palo Alto, Calif.) can also be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding IRS-p53h is inserted within a marker gene sequence, transformed cells containing sequences encoding IRS-p53h can be identified by the absence of marker gene function. Alternatively, a marker gene can be placed in tandem with a sequence encoding IRS-p53h under the control of a single promoter. Expression of the marker gene in response to induction or selection usually indicates expression of the tandem gene as well.

Alternatively, host cells which contain the nucleic acid sequence encoding IRS-p53h and express IRS-p53h may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding IRS-p53h can be detected by DNA-DNA or DNA-RNA hybridization or amplification using probes or fragments or fragments of polynucleotides encoding IRS-p53h. Nucleic acid amplification based assays involve the use of oligonucleotides or oligomers based on the sequences encoding IRS-p53h to detect transformants containing DNA or RNA encoding IRS-p53h.

A variety of protocols for detecting and measuring the expression of IRS-p53h, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on IRS-p53h is preferred, but a competitive binding assay may be employed. These and other assays are well described in the art. (See, e.g., Hampton, R. et al. (1990) *Serological Methods, a Laboratory Manual,* APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding IRS-p53h include oligolabeling, nick translation, end-labeling, or PCR amplification using a labeled nucleotide. Alternatively, the sequences encoding IRS-p53h, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding IRS-p53h may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode IRS-p53h may be designed to contain signal sequences which direct secretion of IRS-p53h through a prokaryotic or eukaryotic cell membrane. Other constructions may be used to join sequences encoding IRS-p53h to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the IRS-p53h encoding sequence may be used to facilitate purification. One such expression vector provides for expression of a fusion protein containing IRS-p53h and a nucleic acid encoding 6 histidine residues preceding a thioredoxin or an enterokinase cleavage site. The histidine residues facilitate purification on immobilized metal ion affinity chromatography (IMAC). (See, e.g., Porath, J. et al. (1992) Prot. Exp. Purif. 3: 263–281.) The enterokinase cleavage site provides a means for purifying IRS-p53h from the fusion protein. (See, e.g., Kroll, D. J. et al. (1993) DNA Cell Biol. 12:441–453.)

Fragments of IRS-p53h may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A Peptide Synthesizer (Perkin Elmer). Various fragments of IRS-p53h may be synthesized separately and then combined to produce the full length molecule.

Therapeutics

Chemical and structural homology exits between IRS-p53h and IRS p53 from hamster (GI 1203820). In addition, IRS-p53h is expressed in reproductive, brain, gastrointestinal, and lung tissues, and in Alzheimer's disease. Therefore, IRS-p53h appears to play a role in reproductive disorders, Alzheimer's disease, cancer, immunological disorders, and disorders associated with insulin response.

In particular, increased expression or activity of IRS-p53h appears to be associated with cancer or immunological disorders, and decreased expression or activity of IRS-p53h with a role in disorders associated with insulin response.

Therefore, in one embodiment, IRS-p53h or a fragment or derivative thereof may be administered to a subject to treat a disorder associated with insulin response. Such a disorder may include, but is not limited to, type 2 (non-insulin-dependent) diabetes mellitus, hyperglycemia, myotonic muscular dystrophy, acanthosis nigricans, retinopathy, nephropathy, atherosclerotic coronary and peripheral arterial disease, and peripheral and autonomic neuropathies.

In another embodiment, a vector capable of expressing IRS-p53h, or a fragment or a derivative thereof, may also be administered to a subject to treat a disorder associated with insulin response, including but not limited to those listed above.

In a further embodiment, a pharmaceutical composition comprising a substantially purified IRS-p53h in conjunction with a suitable pharmaceutical carrier may be administered to a subject to treat or prevent a reproductive disorder including, but not limited to, those provided above.

In still another embodiment, an agonist of IRS-p53h may also be administered to a subject to treat a disorder associated with insulin response, including but not limited to those listed above.

In another embodiment, an antagonist of IRS-p53h may be administered to a subject to treat or prevent a reproductive disorder. Such a reproductive disorder may include, but is not limited to, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, uterine fibroids, fibrocystic breast disease, galactorrhea; disruptions of spermatogenesis, abnormal sperm physiology, cancer of the testis, cancer of the prostate, benign prostatic hyperplasia, prostatitis, Peyronie's disease, carcinoma of the male breast and gynecomastia. In one aspect, an antibody which specifically binds IRS-p53h may be used directly as an antagonist or indirectly as a targeting or delivery mechanism for bringing a pharmaceutical agent to cells or tissue which express IRS-p53h.

In an additional embodiment, a vector expressing the complement of the polynucleotide encoding IRS-p53h may be administered to a subject to treat or prevent a reproductive disorder including, but not limited to, those described above.

In another embodiment, an antagonist of IRS-p53h may be administered to a subject to treat or prevent Alzheimer's disease. In one aspect, an antibody which specifically binds IRS-p53h may be used directly as an antagonist or indirectly as a targeting or delivery mechanism for bringing a pharmaceutical agent to cells or tissue which express IRS-p53h.

In an additional embodiment, a vector expressing the complement of the polynucleotide encoding IRS-p53h may be administered to a subject to treat or prevent Alzheimer's disease.

In another embodiment, an antagonist of IRS-p53h may be administered to a subject to prevent or treat cancer. Such cancers include, but are not limited to, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, antibodies which specifically bind IRS-p53h may be used directly as an antagonist or indirectly as a targeting or delivery mechanism for bringing a pharmaceutical agent to cells or tissue which express IRS-p53h.

In another embodiment, a vector expressing the complement of the polynucleotide encoding IRS-p53h may be administered to a subject to treat or prevent cancer, including but not limited to the cancers listed above.

In another embodiment, an antagonist of IRS-p53h may be administered to a subject to prevent or treat an immunological disorder. Such an immunological disorder may include, but is not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial immunological disorders, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. In one aspect, antibodies which specifically bind IRS-p53h may be used directly as an antagonist or indirectly as a targeting or delivery mechanism for bringing a pharmaceutical agent to cells or tissue which express IRS-p53h.

In another embodiment, a vector expressing the complement of the polynucleotide encoding IRS-p53h may be administered to a subject to treat or prevent an immune disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of IRS-p53h may be produced using methods which are generally known in the art. In particular, purified IRS-p53h may be used to produce antibodies or to screen libraries of pharmaceutical agents to identify those which specifically bind IRS-p53h. Antibodies to IRS-p53h may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with IRS-p53h or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to IRS-p53h have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of IRS-p53h amino acids may be fused with those of another protein, such as KLH, and antibodies to the chimeric molecule may be produced.

Monoclonal antibodies to IRS-p53h may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce IRS-p53h-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for IRS-p53h may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between IRS-p53h and its specific antibody. A two-site, monoclonal-based immunoassay utilizing monoclonal antibodies reactive to two non-interfering IRS-p53h epitopes is preferred, but a competitive binding assay may also be employed. (Maddox, supra.)

In another embodiment of the invention, the polynucleotides encoding IRS-p53h, or any fragment or complement thereof, may be used for therapeutic purposes. In one aspect, the complement of the polynucleotide encoding IRS-p53h may be used in situations in which it would be desirable to block the transcription of the mRNA. In particular, cells may be transformed with sequences complementary to polynucleotides encoding IRS-p53h. Thus, complementary molecules or fragments may be used to modulate IRS-p53h activity, or to achieve regulation of gene function. Such technology is now well known in the art, and sense or antisense oligonucleotides or larger fragments can be designed from various locations along the coding or control regions of sequences encoding IRS-p53h.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequences complementary to the polynucleotides of the gene encoding IRS-p53h. (See, e.g., Sambrook, supra; and Ausubel, supra.)

Genes encoding IRS-p53h can be turned off by transforming a cell or tissue with expression vectors which express high levels of a polynucleotide, or fragment thereof, encoding IRS-p53h. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding IRS-p53h. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding IRS-pS3h.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding IRS-p53h. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of IRS-p53h, antibodies to IRS-p53h, and mimetics. agonists, antagonists, or inhibitors of IRS-p53h. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of IRS-p53h, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example IRS-p53h or fragments thereof, antibodies of IRS-p53h, and agonists, antagonists or inhibitors of IRS-p53h, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind IRS-p53h may be used for the diagnosis of disorders characterized by expression of IRS-p53h, or in assays to monitor patients being treated with IRS-p53h or agonists, antagonists, or inhibitors of IRS-p53h. Antibodies useful for diagnostic purposes may be prepared in the same manner as described above for therapeutics. Diagnostic assays for IRS-p53h include methods which utilize the antibody and a label to detect IRS-p53h in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring IRS-p53h, including ELISAs, RIAs, and FACS, are known in the art and provide a basis for diagnosing altered or abnormal levels of IRS-p53h expression. Normal or standard values for IRS-p53h expression are established by combining body fluids or cell extracts taken from normal mammalian subjects, preferably human, with antibody to IRS-p53h under conditions suitable for complex formation. The amount of standard complex formation may be quantitated by various methods, preferably by photometric means. Quantities of IRS-p53h expressed in subject samples, control and disease, from biopsied tissues are compared with the standard values. Deviation between standard and subject values establishes the parameters for diagnosing disease.

In another embodiment of the invention, the polynucleotides encoding IRS-p53h may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of IRS-p53h may be correlated with disease. The diagnostic assay may be used to determine absence, presence, and excess expression of IRS-p53h, and to monitor regulation of IRS-p53h levels during therapeutic intervention.

In one aspect, hybridization with PCR probes which are capable of detecting polynucleotide sequences, including genomic sequences, encoding IRS-p53h or closely related molecules may be used to identify nucleic acid sequences which encode IRS-p53h. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding IRS-p53h, alleles, or related sequences.

Probes may also be used for the detection of related sequences, and should preferably have at least 50% sequence identity to any of the IRS-p53h encoding sequences. The hybridization probes of the subject invention may be DNA or RNA and may be derived from the sequence of SEQ ID NO:2, and SEQ ID NO:4, or from genomic sequences including promoters, enhancers, and introns of the IRS-p53h gene.

Means for producing specific hybridization probes for DNAs encoding IRS-p53h include the cloning of polynucleotide sequences encoding IRS-p53h or IRS-p53h derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups. for example, by radionuclides such as $^{32}P$ or $^{35}S$, or by enzymatic labels, such as alkaline phosphatase coupled to the probe via avidin/biotin coupling systems, and the like.

Polynucleotide sequences encoding IRS-p53h may be used for the diagnosis of a disorder associated with expression of IRS-p53h. Examples of such a disorder include, but are not limited to, a disorder associated with insulin response such as type 2 (non-insulin-dependent) diabetes mellitus, hyperglycemia, myotonic muscular dystrophy, acanthosis nigricans, retinopathy, nephropathy, atherosclerotic coronary and peripheral arterial disease, and peripheral and autonomic neuropathies; a reproductive disorder such as, disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, autoimmune disorders, ectopic pregnancy, and teratogenesis; cancer of the breast, uterine fibroids, fibrocystic breast disease, galactorrhea; disruptions of spermatogenesis, abnormal sperm physiology, cancer of the testis, cancer of the prostate, benign prostatic hyperplasia, prostatitis, Peyronie's disease, carcinoma of the male breast and gynecomastia; Alzheimer's disease; a cancer such as, adenocarcinoma, leukemia, lymphoma, melanoma, myeloma, sarcoma, and teratocarcinoma, and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and an immunological disorder such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial immunological disorders, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma. The polynucleotide sequences encoding IRS-p53h may be used in Southern or northern analysis, dot blot, or other membrane-based technologies; in PCR technologies; in dipstick, pin, and ELISA assays; and in microarrays utilizing fluids or tissues from patients to detect altered IRS-p53h expression. Such qualitative or quantitative methods are well known in the art.

In a particular aspect, the nucleotide sequences encoding IRS-p53h may be useful in assays that detect the presence of associated disorders, particularly those mentioned above. The nucleotide sequences encoding IRS-p53h may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding IRS-p53h in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of IRS-p53h, a normal or standard profile for expression is established. This may be accomplished by combining body fluids or cell extracts taken from normal subjects, either animal or human, with a sequence, or a fragment thereof, encoding IRS-p53h, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding IRS-p53h may involve the use of PCR. These oligomers may be chemically synthesized, generated enzymatically, or produced in vitro. Oligomers will preferably contain a fragment of a polynucleotide encoding IRS-p53h, or a fragment of a polynucleotide complementary to the polynucleotide encoding IRS-p53h, and will be employed under optimized conditions for identification of a specific gene or condition. Oligomers may also be employed under less stringent conditions for detection or quantitation of closely related DNA or RNA sequences.

Methods which may also be used to quantitate the expression of IRS-p53h include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding IRS-p53h may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding IRS-p53h on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., AT to 11q22-23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, IRS-p53h, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between IRS-p53h and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with IRS-p53h, or fragments thereof, and washed. Bound IRS-p53h is then detected by methods well known in the art. Purified IRS-p53h can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding IRS-p53h specifically compete with a test compound for binding IRS-p53h. In this manner, antibodies can be used to detect the presence of any peptide which shares one or more antigenic determinants with IRS-p53h.

In additional embodiments, the nucleotide sequences which encode IRS-p53h may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

BRSTNOT04

The BRSTNOT04 cDNA library was constructed from microscopically normal breast tissue removed from a 62-year-old female (specimen # 0116A) during unilateral extended simple mastectomy following diagnosis of invasive grade 3 (of 4), nuclear grade 2 (of 3) mammary ductal carcinoma. The surgical margins were found negative for tumor. Also, a 0.4 cm focus of in situ carcinoma was identified in the lower quadrant of the breast. Prior to surgery, the patient was diagnosed with benign hypertension, cerebrovascular disease, atherosclerosis, hyperlipidemia, and hematuria. The patient family history included liver cancer in a sibling.

The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.0, precipitated using 0.3 M sodium acetate and 2.5 volumes of ethanol, resuspended in RNAse-free water, and treated with DNase at 37° C. RNA extraction and precipitation were repeated as before. The mRNA was then isolated with the Qiagen Oligotex kit (QIAGEN, Inc.; Chatsworth, Calif.) and used to construct the cDNA library.

The mRNA was handled according to the recommended protocols in the SuperScript plasmid system (Catalog #18248-013; Gibco-BRL). cDNA synthesis was initiated with a NotI-oligo d(T) primer. Double-stranded cDNA was blunted, ligated to SalI adaptors, digested with NotI, fractionated on a Sepharose CL4B column (Catalog #275105-01; Pharmacia Upjohn), and those cDNAs exceeding 400 bp were ligated into the NotI and SalI sites of the vector pSport I. The plasmid pSport I was subsequently transformed into DH5α™ competent cells (Catalog #18258-012; Gibco-BRL).

ADRETUT05

The ADRETUT05 cDNA library was constructed from tumor tissue obtained from the right adrenal gland of a 52 year-old Caucasian female (specimen # 0058) during a unilateral adrenalectomy. Pathology indicated a pheochromocytoma. Patient history included benign hypertension, depressive disorder, chronic sinusitis, idiopathic proctocolitis, urinary tract infection and irritable colon. Family history included benign hypertension in a sibling, cerebrovascular disease, secondary Parkinsonism, and irritable colon in the mother; atherosclerotic coronary artery disease, hyperlipidemia and malignant brain neoplasm in siblings, and secondary Parkinsonism in the father.

The frozen tissue was homogenized and lysed in Trizol reagent (1 g tissue/10 ml Trizol; Catalog # 10296-028; Gibco-BRL), a monoplastic solution of phenol and guanidine isothiocyanate, using a Brinkmann Homogenizer Polytron PT-3000 (Brinkmann Instruments, Westbury, N.Y.). After a brief incubation on ice, chloroform was added (1:5 v/v) and the lysate was centrifuged. The upper layer was removed to a fresh tube and the RNA extracted with isopropanol, resuspended in DEPC-treated water, and treated with DNase for 25 minutes at 37° C. RNA was extracted and precipitated as before. The mRNA was isolated using the Qiagen Oligotex kit (QIAGEN, Inc., Chatsworth, Calif.) and used to construct the cDNA library.

The mRNA was handled according to the recommended protocols in the SuperScript plasmid system (Catalog # 18248-013, Gibco-BRL). cDNA synthesis was initiated with NotI-oligo d(T) primer. Double-stranded cDNA was blunted, ligated to EcoRI adaptors, digested with NotI, fractionated on a Sepharose CL4B column (Catalog # 275105-01; Pharmacia Upjohn), and those cDNAs exceeding 400 bp were ligated into the NotI and EcoRI sites of the pINCY 1 vector (Incyte). The plasmid pINCY 1 was subsequently transformed into DH5α™ competent cells (Catalog # 18258-012; Gibco-BRL).

II Isolation and Sequencing of cDNA Clones

Plasmid DNA was released from the cells and purified using the REAL Prep 96 plasmid kit (Catalog # 26173; QIAGEN, Inc.). The recommended protocol was employed except for the following changes: 1) the bacteria were cultured in 1 ml of sterile Terrific Broth (Catalog # 22711, Gibco-BRL) with 25 mg/l carbenicillin, 0.4% glycerol; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975; J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity.

Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

Additionally, sequences identified from cDNA libraries may be analyzed to identify those gene sequences encoding conserved protein motifs using an appropriate analysis program, e.g., the Block 2 Bioanalysis Program (Incyte, Palo Alto, Calif.). This motif analysis program, based on sequence information contained in the Swiss-Prot Database and PROSITE, is a method of determining the function of uncharacterized proteins translated from genomic or cDNA sequences. (See, e.g., Bairoch, A. et al. (1997) Nucleic Acids Res. 25:217–221; and Attwood, T. K. et al. (1997) J. Chem. Inf. Comput. Sci. 37:417–424.) PROSITE may be used to identify common functional or structural domains in divergent proteins. The method is based on weight matrices. Motifs identified by this method are then calibrated against the SWISS-PROT database in order to obtain a measure of the chance distribution of the matches.

In another alternative, Hidden Markov models (HMMs) may be used to find protein domains, each defined by a dataset of proteins known to have a common biological function. (See, e.g., Pearson, W. R. and D. J. Lipman (1988) Proc. Natl. Acad. Sci. 85:2444–2448; and Smith, T. F. and M. S. Waterman (1981) J. Mol. Biol. 147:195–197.) HMMs were initially developed to examine speech recognition patterns, but are now being used in a biological context to analyze protein and nucleic acid sequences as well as to model protein structure. (See, e.g., Krogh, A. et al. (1994) J. Mol. Biol. 235:1501–1531; and Collin, M. et al. (1993) Protein Sci. 2:305–314.) HMMs have a formal probabilistic basis and use position-specific scores for amino acids or nucleotides. The algorithm continues to incorporate information from newly identified sequences to increase its motif analysis capabilities.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding IRS-p53h occurs. Abundance and percent abundance are also reported. Abundance directly reflects the number of times a particular transcript is represented in a cDNA library, and percent abundance is abundance divided by the total number of sequences examined in the cDNA library.

V. Extension of IRS-p53h Encoding Polynucleotides

The nucleic acid sequences of Incyte Clones 918158 and 2493150 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier Thermal Cycler (PTC200; M.J. Research, Watertown, Mass.), beginning with 40 pmol of each primer and the recommended concentrations of all other components of the kit, with the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQuick™ (QIAGEN Inc.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2×carb). The following day, several colonies were randomly picked from each plate and cultured in 150 μl of liquid LB/2×Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:2, and SEQ ID NO:4, are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2, and SEQ ID NO:4, are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 (National Biosciences) and labeled by combining 50 pmol of each oligomer, 250 μCi of [γ-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex G-25 superfine resin column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba1, or Pvu II (DuPont NEN, Boston, Mass.).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena. M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VII. Complementary Polynucleotides

Sequences complementary to the IRS-p53h-encoding sequences, or any parts thereof, are used to detect, decrease, or inhibit expression of naturally occurring IRS-p53h. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of IRS-p53h. To inhibit transcription, a complementary oligonucleotide is designed from the most unique 5' sequence and used to prevent promoter binding to the coding sequence. To inhibit translation, a complementary oligonucleotide is designed to prevent ribosomal binding to the IRS-p53h-encoding transcript.

IX. Expression of IRS-p53h

Expression of IRS-p53h is accomplished by subcloning the cDNA into an appropriate vector and transforming the vector into host cells. This vector contains an appropriate promoter, e.g., β-galactosidase, upstream of the cloning site, operably associated with the cDNA of interest. (See, e.g., Sambrook, supra, pp. 404–433; and Rosenberg, M. et al. (1983) Methods Enzymol. 101:123–138.)

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of IRS-p53h into bacterial growth media which can be used directly in the following assay for activity.

X Demonstration of IRS-p53h Activity

Human IR is expressed in and partially purified from chinese hamster ovary cells or rat hepatoma cells as described by Yeh, et al. (supra). IRS-p53h is incubated with the partially purified human IR in the presence of 1 μM insulin, 5 mM MgCl$_2$, 5 mM MnCl$_2$, 0.5 mM ATP in 20 mM HEPES pH 7.5, 0.1% Triton X-100 for 20 min at 25° C. The incubations are subjected to SDS-PAGE electrophoresis (Sambrook, supra). Tyrosine-phosphorylated IRS-p53h is detected by western blotting (Sambrook, supra) using a horseradish peroxidase-conjugated anti-phosphotyrosine antibody such as RC20 (Transduction Laboratories; Lexington, Ky.) and the ECL detection system (Amersham International).

XI Production of IRS-p53h Specific Antibodies

IRS-p53h substantially purified using PAGE electrophoresis (see, e.g., Harrington, M. G. (1990) Methods Enzymol. 182:488–495), or other purification techniques, is used to immunize rabbits and to produce antibodies using standard protocols.

Alternatively, the IRS-p53h amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring IRS-p53h Using Specific Antibodies

Naturally occurring or recombinant IRS-p53h is substantially purified by immunoaffinity chromatography using antibodies specific for IRS-p53h. An immunoaffinity column is constructed by covalently coupling anti-IRS-p53h antibody to an activated chromatographic resin, such as CNBr-activated Sepharose (Pharmacia & Upjohn). After the coupling, the resin is blocked and washed according to the manufacturer's instructions.

Media containing IRS-p53h are passed over the immunoaffinity column, and the column is washed under conditions that allow the preferential absorbance of IRS-p53h (e.g., high ionic strength buffers in the presence of detergent). The column is eluted under conditions that disrupt antibody/IRS-p53h binding (e.g., a buffer of pH 2 to pH 3, or a high concentration of a chaotrope, such as urea or thiocyanate ion), and IRS-p53h is collected.

XIII. Identification of Molecules which Interact with IRS-p53h

IRS-p53h, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled IRS-p53h, washed, and any wells with labeled IRS-p53h complex are assayed. Data obtained using different concentrations of IRS-p53h are used to calculate values for the number, affinity, and association of IRS-p53h with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 534 amino acids
      (B) TYPE: amino acid
      (C) STRANDEDNESS: single
      (D) TOPOLOGY: linear (vii) IMMEDIATE SOURCE:
      (A) LIBRARY: ADRETUT05
      (B) CLONE: 2493150

(xi) SEQUENCE DESCRIPTION: SEQ ID NO:1:

Met Ser Leu Ser Arg Ser Glu Glu Met His Arg Leu Thr Glu Asn Val
 1          5                10              15

Tyr Lys Thr Ile Met Glu Gln Phe Asn Pro Ser Leu Arg Asn Phe Ile

-continued

```
                20                  25                  30
Ala Met Gly Lys Asn Tyr Glu Lys Ala Leu Ala Gly Val Thr Tyr Ala
            35                  40                  45
Ala Lys Gly Tyr Phe Asp Ala Leu Val Lys Met Gly Glu Leu Ala Ser
 50                  55                  60
Glu Ser Gln Gly Ser Lys Glu Leu Gly Asp Val Leu Phe Gln Met Ala
 65                  70                  75                  80
Glu Val His Arg Gln Ile Gln Asn Gln Leu Glu Glu Met Leu Lys Ser
                85                  90                  95
Phe His Asn Glu Leu Leu Thr Gln Leu Glu Gln Lys Val Glu Leu Asp
                100                 105                 110
Ser Arg Tyr Leu Ser Ala Ala Leu Lys Lys Tyr Gln Thr Glu Gln Arg
            115                 120                 125
Ser Lys Gly Asp Ala Leu Asp Lys Cys Gln Ala Glu Leu Lys Lys Leu
            130                 135                 140
Arg Lys Lys Ser Gln Gly Ser Lys Asn Pro Gln Lys Tyr Ser Asp Lys
145                 150                 155                 160
Glu Leu Gln Tyr Ile Asp Ala Ile Ser Asn Lys Gln Gly Glu Leu Glu
                165                 170                 175
Asn Tyr Val Ser Asp Gly Tyr Lys Thr Ala Leu Thr Glu Glu Cys Arg
            180                 185                 190
Arg Phe Cys Phe Leu Val Glu Lys Gln Cys Ala Val Ala Lys Asn Ser
            195                 200                 205
Ala Ala Tyr His Ser Lys Gly Lys Glu Leu Leu Pro Gln Lys Leu Pro
            210                 215                 220
Leu Trp Gln Gln Ala Cys Ala Asp Pro Ser Lys Ile Pro Glu Arg Ala
225                 230                 235                 240
Val Gln Leu Met Gln Gln Val Ala Ser Asn Gly Ala Thr Leu Pro Ser
                245                 250                 255
Ala Leu Ser Ala Ser Lys Ser Asn Leu Val Ile Ser Asp Pro Ile Pro
            260                 265                 270
Gly Ala Lys Pro Leu Pro Val Pro Pro Glu Leu Ala Pro Phe Val Gly
            275                 280                 285
Arg Met Ser Ala Gln Glu Ser Thr Pro Ile Met Asn Gly Val Thr Gly
            290                 295                 300
Pro Asp Gly Glu Asp Tyr Ser Pro Trp Ala Asp Arg Lys Ala Ala Gln
305                 310                 315                 320
Pro Lys Ser Leu Ser Pro Pro Gln Ser Gln Ser Lys Leu Ser Asp Ser
            325                 330                 335
Tyr Ser Asn Thr Leu Pro Val Arg Lys Ser Val Thr Pro Lys Asn Ser
            340                 345                 350
Tyr Ala Thr Thr Glu Asn Lys Thr Leu Pro Arg Ser Ser Ser Met Ala
            355                 360                 365
Ala Gly Leu Glu Arg Asn Gly Arg Met Arg Val Lys Ala Ile Phe Ser
            370                 375                 380
His Ala Ala Gly Asp Asn Ser Thr Leu Leu Ser Phe Lys Glu Gly Asp
385                 390                 395                 400
Leu Ile Thr Leu Leu Val Pro Glu Ala Arg Asp Gly Trp His Tyr Gly
                405                 410                 415
Glu Ser Glu Lys Thr Lys Met Arg Gly Trp Phe Pro Phe Ser Tyr Thr
            420                 425                 430
Arg Val Leu Asp Ser Asp Gly Ser Asp Arg Leu Arg Met Ser Leu Gln
            435                 440                 445
```

```
Gln Gly Lys Ser Ser Ser Thr Gly Asn Leu Leu Asp Lys Asp Asp Leu
    450                 455                 460

Ala Ser Pro Pro Asp Tyr Gly Ala Ala Ser Arg Ala Phe Pro Ala
465                 470                 475                 480

Gln Thr Ala Ser Gly Phe Lys Gln Arg Pro Tyr Ser Val Ala Val Pro
                485                 490                 495

Ala Phe Ser Gln Gly Leu Asp Asp Tyr Gly Ala Arg Ser Met Ser Arg
                500                 505                 510

Asn Pro Phe Ala His Val Gln Leu Lys Pro Thr Val Thr Asn Asp Arg
            515                 520                 525

Ser Ala Pro Leu Leu Ser
    530
```

(2) INFORMATION FOR SEQ ID NO:2:

(i) SEQUENCE CHARACTERISTICS:
        (A) LENGTH: 2080 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT06
        (B) CLONE: 918158

(xi) SEQUENCE DESCRIPTION: SEQ ID NO:2:

```
GTCCGCTTTC GTCTCCGTCC TGCTGCCGTT ACCGCCGCTG CTGCCGCCGC TTGCGTCCCC    60

CGCTCCGGTC TGTGGTGCAG CCGGGACCCA GGACCATGTC TCTGTCTCGC TCAGAGGAGA   120

TGCACCGGCT CACGGAAAAT GTCTATAAGA CCATCATGGA GCAGTTCAAC CCTAGCCTCC   180

GGAACTTCAT CGCCATGGGG AAGAATTACG AGAAGGCACT GGCAGGTGTG ACGTATGCAG   240

CCAAAGGCTA CTTTGACGCC CTGGTGAAGA TGGGGGAGCT GGCCAGCGAG AGCCAGGGCT   300

CCAAAGAACT CGGAGACGTT CTCTTCCAGA TGGCTGAAGT CCACAGGCAG ATCCAGAATC   360

AGCTGGAAGA AATGCTGAAG TCTTTTCACA ACGAGCTGCT TACGCAGCTG GAGCAGAAGG   420

TGGAGCTGGA CTCCAGGTAT CTGAGTGCTG CGCTAAAGAA ATACCAGACT GAGCAAAGGA   480

GCAAAGGCGA CGCCCTGGAC AAGTGTCAGG CTGAGCTGAA GAAGCTTCGG AAGAAGAGCC   540

AGGGCAGCAA GAATCCTCAG AAGTACTCGG ACAAGGAGCT GCAGTACATC GACGCCATCA   600

GCAACAAGCA GGGCGAGCTG GAGAATTACG TGTCCGACGG CTACAAGACC GCACTGACAG   660

AGGAGTGCAG GCGCTTCTGC TTCCTGGTGG AGAAGCAGTG CGCCGTGGCC AAGAACTCCG   720

CGGCCTACCA CTCCAAGGGC AAGGAGCTGC TGCCGCAGAA GCTGCCGCTG TGGCAACAGG   780

CCTGTGCCGA CCCCAGCAAG ATCCCGGAGC GCGCGGTGCA GCTCATGCAG CAGGTGGCCA   840

GCAACGGCGC CACCCTCCCC AGCGCCCTGT CGGCCTCCAA GTCCAACCTG GTCATTTCCG   900

ACCCCATTCC GGGGGCCAAG CCCCTGCCGG TGCCCCCCGA GCTGGCACCG TTCGTGGGGC   960

GGATGTCTGC CCAGGAGAGC ACACCCATCA TGAACGGCGT CACAGGCCCG GATGGCGAGG  1020

ACTACAGCCC GTGGGCTGAC CGCAAGGCTG CCCAGCCCAA ATCCCTGTCT CCTCCGCAGT  1080

CTCAGAGCAA GCTCAGCGAC TCCTACTCCA ACACACTCCC CGTGCGCAAG AGCGTGACCC  1140

CAAAAAACAG CTATGCCACC ACCGAGAACA AGACTCTGCC TCGCTCGAGC TCCATGGCAG  1200

CCGGCCTGGA GCGCAATGGC CGTATGCGGG TGAAGGCCAT CTTCTCCCAC GCTGCTGGGG  1260

ACAACAGCAC CCTCCTGAGC TTCAAGGAGG GTGACCTCAT TACCCTGCTG GTGCCTGAGG  1320

CCCGCGATGG CTGGCACTAC GGAGAGAGTG AGAAGACCAA GATGCGGGGC TGGTTTCCCT  1380
```

```
TCTCCTACAC CCGGGTCTTG ACAGCGATG GCAGTGACAG GCTGCGCATG AGCCTGCAGC   1440

AAGGGAAGAG CAGCAGCACG GGCAACCTCC TGGACAAGGA CGACCTGGCC AGCCCACCCC   1500

CCGATTACGG CGCCGCCTCC CGGGCTTTCC CCGCCCAGAC GGCCAGCGGC TTCAAGCAGA   1560

GGCCCTACAG TGTGGCCGTG CCCGCCTTCT CCCAGGGCCT GGATGACTAT GGAGCGCGGT   1620

CCATGAGCAG GAATCCCTTT GCCCACGTCC AGCTGAAGCC GACAGTGACC AACGACAGGT   1680

CTGCCCCCCT CCTCAGCTGA TGGCCACATC TGCAGTGCTG CCCATCTGGT GGCTTCCCCC   1740

GCCCTTCCCA TGTAGCCTGT TCTGTCATCA TCTGTGCGTT CCTGTGTAGA GAACATCCAG   1800

GCCCCGGCTG CCTGGTCTTG CCCCACTTGA GTCTGGCCTG GACTGGATTC CAGCTGTTCT   1860

AGGCAGGGCC GGGCAGAGTG GGGCGCAAGC CCTGGATGGC GAGACCCAGT GGCTGGGNCT   1920

GCCAGGGCTG AGGGGCGCT CTTGAAGGTA CACGCTCTGG TCACATGGCA TGGAGCTTGG   1980

GTACCCTGAG TAAGGGAGAA TTTGGCCACT GGTGGCTGGG AGGGAACTTG TTGCCTGCTG   2040

CTCTCCTGCC TAATAAAAAG CTCTCCTGCA AAAAAAAAAT                       2080
```

(2) INFORMATION FOR SEQ ID NO:3:

(i) SEQUENCE CHARACTERISTICS:
        (A) LENGTH: 553 amino acids
        (B) TYPE: amino acid
        (C) STRANDEDNESS: single
        (D) TOPOLOGY: linear (vii) IMMEDIATE SOURCE:
        (A) LIBRARY: ADRETUT05
        (B) CLONE: 2493150

(xi) SEQUENCE DESCRIPTION: SEQ ID NO:3:

```
Met Ser Leu Ser Arg Ser Glu Glu Met His Arg Leu Thr Glu Asn Val
 1               5                  10                  15

Tyr Lys Arg Val Glu Glu Lys Tyr Gln Arg Asn Leu Phe Pro Ile Phe
                20                  25                  30

Ser Pro Ser Ala Leu Lys Pro Glu Ser Arg Asn Phe Arg Gly Glu Ser
            35                  40                  45

Trp Gln Gly Thr Ile Met Glu Gln Phe Asn Pro Ser Leu Arg Asn Phe
    50                  55                  60

Ile Ala Met Gly Lys Asn Tyr Glu Lys Ala Leu Ala Gly Val Thr Tyr
65                  70                  75                  80

Ala Ala Lys Gly Tyr Phe Asp Ala Leu Val Lys Met Gly Glu Leu Ala
                85                  90                  95

Ser Glu Ser Gln Gly Ser Lys Glu Leu Gly Asp Val Leu Phe Gln Met
            100                 105                 110

Ala Glu Val His Arg Gln Ile Gln Asn Gln Leu Glu Glu Met Leu Lys
        115                 120                 125

Ser Phe His Asn Glu Leu Leu Thr Gln Leu Glu Gln Lys Val Glu Leu
    130                 135                 140

Asp Ser Arg Tyr Leu Ser Ala Ala Leu Lys Lys Tyr Gln Thr Glu Gln
145                 150                 155                 160

Arg Ser Lys Gly Asp Ala Leu Asp Lys Cys Gln Ala Glu Leu Lys Lys
                165                 170                 175

Leu Arg Lys Lys Ser Gln Gly Ser Lys Asn Pro Gln Lys Tyr Ser Asp
            180                 185                 190

Lys Glu Leu Gln Tyr Ile Asp Ala Ile Ser Asn Lys Gln Gly Glu Leu
        195                 200                 205
```

-continued

```
Glu Asn Tyr Val Ser Asp Gly Tyr Lys Thr Ala Leu Thr Glu Glu Arg
    210                 215                 220

Arg Arg Phe Cys Phe Leu Val Glu Lys Gln Cys Ala Val Ala Lys Asn
225                 230                 235                 240

Ser Ala Ala Tyr His Ser Lys Gly Lys Glu Leu Leu Pro Gln Lys Leu
                245                 250                 255

Pro Leu Trp Gln Gln Ala Cys Ala Asp Pro Ser Lys Ile Pro Glu Arg
            260                 265                 270

Ala Val Gln Leu Met Gln Gln Val Ala Ser Asn Gly Ala Thr Leu Pro
        275                 280                 285

Ser Ala Leu Ser Ala Ser Lys Ser Asn Leu Val Ile Ser Asp Pro Ile
    290                 295                 300

Pro Gly Ala Lys Pro Leu Pro Val Pro Pro Glu Leu Ala Pro Phe Val
305                 310                 315                 320

Gly Arg Met Ser Ala Gln Glu Ser Thr Pro Ile Met Asn Gly Val Thr
                325                 330                 335

Gly Pro Asp Gly Glu Asp Tyr Ser Pro Trp Ala Asp Arg Lys Ala Ala
            340                 345                 350

Gln Pro Lys Ser Leu Ser Pro Gln Ser Gln Ser Lys Leu Ser Asp
        355                 360                 365

Ser Tyr Ser Asn Thr Leu Pro Val Arg Lys Ser Val Thr Pro Lys Asn
    370                 375                 380

Ser Tyr Ala Thr Thr Glu Asn Lys Thr Leu Pro Arg Ser Ser Ser Met
385                 390                 395                 400

Ala Ala Gly Leu Glu Arg Asn Gly Arg Met Arg Val Lys Ala Ile Phe
                405                 410                 415

Ser His Ala Ala Gly Asp Asn Ser Thr Leu Leu Ser Phe Lys Glu Gly
            420                 425                 430

Asp Leu Ile Thr Leu Leu Val Pro Glu Ala Arg Asp Gly Trp His Tyr
        435                 440                 445

Gly Glu Ser Glu Lys Thr Lys Met Arg Gly Trp Phe Pro Phe Ser Tyr
    450                 455                 460

Thr Arg Val Leu Asp Ser Asp Gly Ser Asp Arg Leu His Met Ser Leu
465                 470                 475                 480

Gln Gln Gly Lys Ser Ser Thr Gly Asn Leu Leu Asp Lys Asp Asp
                485                 490                 495

Leu Ala Ile Pro Pro Pro Asp Tyr Gly Ala Ala Ser Arg Ala Phe Pro
            500                 505                 510

Ala Gln Thr Ala Ser Gly Phe Lys Gln Arg Pro Tyr Ser Val Ala Val
        515                 520                 525

Pro Ala Phe Ser Gln Gly Leu Asp Asp Tyr Gly Ala Arg Ser Met Ser
    530                 535                 540

Ser Ala Asp Val Glu Val Ala Arg Phe
545                 550
```

(2) INFORMATION FOR SEQ ID NO:4:

(i) SEQUENCE CHARACTERISTICS:
        (A) LENGTH: 2328 base pairs
        (B) TYPE: nucleic acid
        (C) STRANDEDNESS: single
        (D) TOPOLOGY: linear (vii) IMMEDIATE SOURCE:
        (A) LIBRARY: ADRETUT05
        (B) CLONE: 2493150

(xi) SEQUENCE DESCRIPTION: SEQ ID NO:4:

```
CGCTTGCTTG GCATTTGGAC ATCTACGGCT GGAATTCCGG GTCGACCCAC GCGTCCGGTC      60

CGCTTTCGTC TCCGTCCTGC TGCCGTTACC GCCGCTGCTG CCGCCGCTTG CGTCCCCCGC     120

TCCGGTCTGT GGTGCAGCCG GGACCCAGGA CCATGTCTCT GTCTCGCTCA GAGGAGATGC     180

ACCGGCTCAC GGAAAATGTC TATAAGAGGG TGGAAGAGAA GTACCAGCGG AACCTTTTTC     240

CTATTTTTTC TCCTTCTGCG CTGAAACCAG AAAGCAGGAA CTTTCGTGGT GAGAGTTGGC     300

AGGGGACCAT CATGGAGCAG TTCAACCCTA GCCTCCGGAA CTTCATCGCC ATGGGGAAGA     360

ATTACGAGAA GGCACTGGCA GGTGTGACGT ATGCAGCCAA AGGCTACTTT GACGCCCTGG     420

TGAAGATGGG GGAGCTGGCC AGCGAGAGCC AGGGCTCCAA GAACTCGGA GACGTTCTCT      480

TCCAGATGGC TGAAGTCCAC AGGCAGATCC AGAATCAGCT GGAAGAAATG CTGAAGTCTT     540

TTCACAACGA GCTGCTTACG CAGCTGGAGC AGAAGGTGGA GCTGGACTCC AGGTATCTGA     600

GTGCTGCGCT GAAGAAATAC CAGACTGAGC AAAGGAGCAA AGGCGACGCC CTGGACAAGT     660

GTCAGGCTGA GCTGAAGAAG CTTCGGAAGA GAGCCAGGG CAGCAAGAAT CCTCAGAAGT      720

ACTCGGACAA GGAGCTGCAG TACATCGACG CCATCAGCAA CAAGCAGGGC GAGCTGGAGA     780

ATTACGTGTC CGACGGCTAC AAGACCGCAC TGACAGAGGA GCGCAGGCGC TTCTGCTTCC     840

TGGTGGAGAA GCAGTGCGCC GTGGCCAAGA ACTCCGCGGC CTACCACTCC AAGGGCAAGG     900

AGCTGCTGCC GCAGAAGCTG CCGCTGTGGC AACAGGCCTG TGCCGACCCC AGCAAGATCC     960

CGGAGCGCGC GGTGCAGCTC ATGCAGCAGG TGGCCAGCAA CGGCGCCACC CTCCCCAGCG    1020

CCCTGTCGGC CTCCAAGTCC AACCTGGTCA TTTCCGACCC CATTCCGGGG GCCAAGCCCC    1080

TGCCGGTGCC CCCCGAGCTG GCACCGTTCG TGGGGCGGAT GTCTGCCCAG GAGAGCACAC    1140

CCATCATGAA CGGCGTCACA GGCCCGGATG GCGAGGACTA CAGCCCGTGG GCTGACCGCA    1200

AGGCTGCCCA GCCCAAATCC CTGTCTCCTC CGCAGTCTCA GAGCAAGCTC AGCGACTCCT    1260

ACTCCAACAC ACTCCCCGTG CGCAAGAGCG TGACCCCAAA AAACAGCTAT GCCACCACCG    1320

AGAACAAGAC TCTGCCTCGC TCGAGCTCCA TGGCAGCCGG CCTGGAGCGC AATGGCCGTA    1380

TGCGGGTGAA GGCCATCTTC TCCCACGCTG CTGGGACAA CAGCACCCTC CTGAGCTTCA     1440

AGGAGGGTGA CCTCATTACC CTGCTGGTGC CTGAGGCCCG CGATGGCTGG CACTACGGAG    1500

AGAGTGAGAA GACCAAGATG CGGGGCTGGT TTCCCTTCTC CTACACCCGG GTCTTGGACA    1560

GCGATGGCAG TGACAGGCTG CACATGAGCC TGCAGCAAGG GAAGAGCAGC AGCACGGGCA    1620

ACCTCCTGGA CAAGGACGAC CTGGCCATCC ACCCCCCGA TTACGGCGCC GCCTCCCGGG     1680

CCTTCCCCGC CCAGACGGCC AGCGGCTTCA GCAGAGGCC CTACAGTGTG GCCGTGCCCG    1740

CCTTCTCCCA GGGCCTGGAT GACTATGGAG CGCGGTCCAT GAGCAGCGCC GATGTGGAAG    1800

TGGCCAGATT CTGAGCCGCC TGACTAGAGT TAGAATCCCT TTGCCCACGT CCAGCTGAAG    1860

CCGACAGTGA CCAACGACAG GTCTGCCCCC CTCCTCAGCT GATGGCCACA TCTGCAGTGC    1920

TGCCCATCTG GTGGCTTCCC CCGCCCTTCC CATGTAGCCT GTTCTGTCAT CATCTGTGCG    1980

TTCCTGTGTA GAGAACATCC AGGCCCCGGC TGCCTGGTCT TGCCCCACTT GAGTCTGGCC    2040

TGGACTGGAT CCCAGCTGTT CTAGGCAGGG CCGGGCAGAG TGGGCGCAG GCCCCTGAAG     2100

GGCGAGACCC AGTGGCTGGG CTGCCCAGGG CTGAGGGGCC GCCTCTTGAG GGTACACGCC    2160

TCTGGTCACA TGGCCATGGA GCCTTGGGTA CCCCTGAGTT AAGGGAGGAC ATTTGGCCAG    2220

CTGGTGGCTG GGAGGGGAGC CTGGCTGCCC TGCTGCTTCT CCTGCCTAAT AAACAGGCTT    2280

CTCCTGCAAA AAAAAAAAA AAAGAAAAA AGAGAGGAGG GAGAGGAT                   2328
```

(2) INFORMATION FOR SEQ ID NO:5:

(i) SEQUENCE CHARACTERISTICS:
        (A) LENGTH: 521 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1203820

(xi) SEQUENCE DESCRIPTION: SEQ ID NO:5:

```
Met Ser Leu Ser Arg Ser Glu Glu Met His Arg Leu Thr Glu Asn Val
  1               5                  10                  15

Tyr Lys Thr Ile Met Glu Gln Phe Asn Pro Ser Leu Arg Asn Phe Ile
                 20                  25                  30

Ala Met Gly Lys Asn Tyr Glu Lys Ala Leu Ala Gly Val Thr Phe Ala
             35                  40                  45

Ala Lys Gly Tyr Phe Asp Ala Leu Val Lys Met Gly Glu Leu Ala Ser
         50                  55                  60

Glu Ser Gln Gly Ser Lys Glu Leu Gly Asp Val Leu Phe Gln Met Ala
 65                  70                  75                  80

Glu Val His Arg Gln Ile Gln Asn Gln Leu Glu Met Leu Lys Ser
                 85                  90                  95

Phe His Asn Glu Leu Leu Thr Gln Leu Glu Gln Lys Val Glu Leu Asp
                100                 105                 110

Ser Arg Tyr Leu Ser Ala Ala Leu Lys Lys Tyr Gln Ala Glu Gln Arg
            115                 120                 125

Ser Lys Gly Asp Ala Leu Asp Lys Cys Gln Ala Glu Leu Lys Lys Leu
        130                 135                 140

Arg Lys Lys Ser Gln Gly Ser Lys Asn Pro Gln Lys Tyr Ser Asp Lys
145                 150                 155                 160

Glu Leu Gln Tyr Ile Asp Ala Ile Ser Asn Lys Gln Gly Glu Leu Glu
                165                 170                 175

Asn Tyr Val Ser Asp Gly Tyr Lys Thr Ala Leu Thr Glu Glu Arg Arg
            180                 185                 190

Arg Phe Cys Phe Leu Val Glu Lys Gln Cys Ala Val Ala Lys Asn Ser
        195                 200                 205

Ala Ala Tyr His Ser Lys Gly Lys Glu Leu Leu Ala Gln Lys Leu Pro
    210                 215                 220

Val Trp Gln Gln Ala Cys Ala Asp Pro Asn Lys Ile Pro Asp Arg Ala
225                 230                 235                 240

Val Gln Leu Met Gln Gln Ile Ala Ser Ser Asn Gly Ser Ile Leu Pro
                245                 250                 255

Ser Thr Leu Ser Ala Ser Lys Ser Asn Leu Val Ile Ser Asp Pro Ile
            260                 265                 270

Pro Gly Ala Lys Pro Leu Pro Val Pro Pro Glu Leu Ala Pro Phe Val
        275                 280                 285

Gly Arg Met Ser Ala Gln Glu Asn Val Pro Val Met Asn Gly Val Ala
    290                 295                 300

Gly Pro Asp Ser Glu Asp Tyr Asn Pro Trp Ala Asp Arg Lys Ala Ala
305                 310                 315                 320

Gln Pro Lys Ser Leu Ser Pro Pro Ser Gln Ser Lys Leu Ser Asp
                325                 330                 335
```

```
              -continued

Ser Tyr Ser Asn Thr Leu Pro Val Arg Lys Ser Val Thr Pro Lys Asn
            340                 345                 350

Ser Tyr Ala Thr Thr Glu Asn Lys Thr Leu Pro Arg Ser Ser Ser Met
            355                 360                 365

Ala Ala Gly Leu Glu Arg Asn Gly Arg Met Arg Val Lys Ala Ile Phe
        370                 375                 380

Ser His Ala Ala Gly Asp Asn Ser Thr Leu Leu Ser Phe Lys Glu Gly
385                     390                 395                 400

Asp Leu Ile Thr Leu Leu Val Pro Glu Ala Arg Asp Gly Trp His Tyr
                405                 410                 415

Gly Glu Ser Glu Lys Thr Lys Met Arg Gly Trp Phe Pro Phe Ser Tyr
            420                 425                 430

Thr Arg Val Leu Asp Ser Asp Gly Ser Asp Arg Leu His Met Ser Leu
        435                 440                 445

Gln Gln Gly Lys Ser Ser Thr Gly Asn Leu Leu Asp Lys Asp Asp
            450             455                 460

Leu Ala Val Pro Pro Pro Asp Tyr Gly Thr Ser Ser Arg Ala Phe Pro
465                 470                 475                 480

Thr Gln Thr Ala Gly Thr Phe Lys Gln Arg Pro Tyr Ser Val Ala Val
            485                 490                 495

Pro Ala Phe Ser Gln Gly Leu Asp Asp Tyr Gly Ala Arg Ser Val Ser
            500                 505                 510

Ser Ala Asp Val Glu Val Ala Arg Phe
            515             520
```

What is claimed is:

1. An isolated polypeptide comprising a sequence of SEQ ID NO: 1 or SEQ ID NO: 3.
2. A composition comprising the polypeptide of claim 1 in conjunction with pharmaceutical carrier.
3. An isolated polynucleotide encoding a polypeptide of claim 1.
4. An isolated polynucleotide of claim 3, comprising a sequence of SEQ ID NO: 2 or SEQ ID NO: 4.
5. An expression vector comprising a promoter sequence operably linked to a polynucleotide of claim 3.
6. A host cell transformed with the expression vector of claim 5.
7. A method of producing a polypeptide of claim 1, said method comprising:
   a) culturing a cell under conditions suitable for expression of the polypeptide, wherein said cell is transformed with an expression vector, and said expression vector comprises a promoter sequence operably linked to a polynucleotide encoding the polypeptide of claim 1, and
   b) recovering the polypeptide so expressed.
8. A method of screening for a molecule or compound that specifically binds to the polypeptide of claim 1, said method comprising the steps of:
   a) combining the polypeptide of claim 1 with at least one molecule or compound under suitable conditions, and
   b) detecting binding of the polypeptide of claim 1 to the molecule or compound, thereby identifying a molecule or compound that specifically binds to the polypeptide.
9. The method of claim 8 wherein the molecules or compounds are selected from DNA molecules, RNA molecules, peptide nucleic acids, peptides, proteins, antibodies, immunoglobulins, and drugs.

10. A method of using a protein to prepare and purify antibodies comprising:
   a) immunizing an animal with the protein of claim 1 under conditions to elicit an antibody response;
   b) isolating antibodie from the animal;
   c) attaching the protein to a substrate;
   d) contacting the substrate with isolated antibodies under conditions to allow specific binding to the protein;
   e) dissociating the antibodies from the protein, thereby obtaining purified antibodies.
11. An isolated polynucleotide comprising a sequence selected from the group consisting of:
   a) a polynucleotide of SEQ ID NO: 2 and SEQ ID NO: 4,
   b) a fragment of SEQ ID NO:2 from about nucleotide 1621 to about nucleotide 1647 of SEQ ID NO:2,
   c) a fragment of SEQ ID NO:4 from about nucleotide 295 to about nucleotide 315 of SEQ ID NO:4, and
   d) a polynucleotide sequence completely complementary to a)–c).
12. A method for detecting a polynucleotide in a sample, the method comprising the steps of:
   (a) hybridizing the polynucleotide of claim 11 to at least one of the nucleic acids in the sample, thereby forming a hybridization complex; and
   (b) detecting the hybridization complex, wherein the presence of the hybridization complex correlates with the presence of the polynucleotide encoding the polypeptide in the sample.
13. The method of claim 12 wherein the nucleic acids of the sample are amplified by the polymerase chain reaction prior to hybridization.

* * * * *

UNITED STATES PATENT AND TRADEMARK OFFICE
CERTIFICATE OF CORRECTION

PATENT NO. : 6,589,935 B1
DATED : July 8, 2003
INVENTOR(S) : Hillman et al.

It is certified that error appears in the above-identified patent and that said Letters Patent is hereby corrected as shown below:

Column 52,
Line 38, please replace "antibodie" with -- antibodies --

Signed and Sealed this

Thirtieth Day of September, 2003

JAMES E. ROGAN
*Director of the United States Patent and Trademark Office*